(12) United States Patent
Seipel

(10) Patent No.: US 9,682,115 B2
(45) Date of Patent: Jun. 20, 2017

(54) HERBAL COMPOSITIONS FOR THE PREVENTION OR TREATMENT OF BENIGN PROSTATIC HYPERPLASIA AND RELATED DISORDERS

(71) Applicant: Tracey Anne Seipel, Kelvin Grove (AU)

(72) Inventor: Tracey Anne Seipel, Kelvin Grove (AU)

(73) Assignee: Seipel Group Pty Ltd (AU)

( * ) Notice: Subject to any disclaimer, the term of this patent is extended or adjusted under 35 U.S.C. 154(b) by 0 days.

(21) Appl. No.: 13/800,735

(22) Filed: Mar. 13, 2013

(65) Prior Publication Data

US 2013/0259958 A1     Oct. 3, 2013

Related U.S. Application Data

(60) Provisional application No. 61/619,106, filed on Apr. 2, 2012.

(51) Int. Cl.
| | |
|---|---|
| *A61K 36/11* | (2006.01) |
| *A61K 36/889* | (2006.01) |
| *A61K 36/185* | (2006.01) |
| *A61K 36/54* | (2006.01) |

(52) U.S. Cl.
CPC ............ *A61K 36/889* (2013.01); *A61K 36/11* (2013.01); *A61K 36/185* (2013.01); *A61K 36/54* (2013.01)

(58) Field of Classification Search
None
See application file for complete search history.

(56) References Cited

U.S. PATENT DOCUMENTS

| | | | |
|---|---|---|---|
| 2002/0012712 A1* | 1/2002 | Gregg, Jr. ................... | 424/727 |
| 2006/0040004 A1* | 2/2006 | Seipel ........................ | 424/762 |

FOREIGN PATENT DOCUMENTS

CN          1698837 A    * 11/2005

* cited by examiner

*Primary Examiner* — Terry A McKelvey
*Assistant Examiner* — Catheryne Chen
(74) *Attorney, Agent, or Firm* — Steve P. Hassid; Partners Law Group, Inc.

(57) ABSTRACT

Provided in one embodiment is an herbal composition for the prevention or treatment of disorders of the prostate, for example, benign prostatic hyperplasia (BPH), prostatitis, and prostatic intraepithelial neoplasia, and for overactive bladder (OAB), urinary incontinence (UI), nocturia, poor urinary stream, and straining to urinate associated with these prostate disorders. Specifically one embodiment provides compositions that contain *Crateva nurvala, Equisetum arvense, Lindera aggregata*, and *Serenoa repens*, and methods of use thereof.

15 Claims, 5 Drawing Sheets

HERBAL COMPOSITIONS FOR THE PREVENTION OR TREATMENT OF BENIGN PROSTATIC HYPERPLASIA AND RELATED DISORDERS

CROSS-REFERENCE TO RELATED APPLICATIONS

This application claims the benefit, under 35 U.S.C. §119(e), of U.S. Provisional Ser. No. 61/619,106, filed Apr. 2, 2012, the entire contents of which is hereby incorporated herein by reference.

All publications, patents, and patent applications cited in this Specification are hereby incorporated by reference in their entirety.

BACKGROUND

The prostate is a male reproductive gland. Benign Prostate Hypertrophy (BPH) or prostate enlargement is a condition of aging. According to the National Institutes of Health (NIH), BPH affects more than 50% of men over the age of 60 and as many as 90% of men over the age of 70. The increase in size of the prostate gland that occurs with BPH exerts pressure on the urethra, resulting in obstruction and difficulty with urine flow.

The exact cause of BPH is uncertain. It is possible that the condition is associated with hormonal changes that occur as men age. The testes produce the hormone testosterone, which is converted to dihydrotestosterone (DHT) and estradiol (estrogen) in certain tissues. High levels of dihydrotestosterone, a testosterone derivative involved in prostate growth, may accumulate and cause hypertrophy. How and why levels of DHT increase remain a subject of research. However, approaches to block 5 alpha reductase and therefore the conversion of testosterone to DHT (dihydrotestosterone) are shown to be effective in treating BPH.

The symptoms of BPH result from the impact the prostate enlargement has on the bladder and lower urinary tract. Common symptoms include dribbling after voiding; feeling that the bladder has not emptied completely after urination; frequent urination, particularly at night (i.e., nocturia); a hesitant, interrupted, or weak urine stream caused by decreased force; leakage of urine (i.e., overflow incontinence); the need for pushing or straining to begin urination; recurrent, sudden, urgent need to urinate; irritated bladder or urethra; blood in the urine (i.e., hematuria), caused by straining to void.

Prostatitis is a term that describes inflammatory conditions of the prostate gland. Bacterial infections are the cause in many cases, but evidence of infection is not always found. Prostatitis can affect men of any age and it is estimated that 50% of men experience the disorder during their lifetime. Prostatitis is the most common urological disorder in men over the age of 50 years old and the third most common disorder in men younger than 50 years old. There are four types of prostatitis: acute bacterial prostatitis (ABP) is inflammation of the prostate gland caused by bacteria such as *Escherichia coli* and *Klebsiella*; chronic bacterial prostatitis (CBP) is a recurrent infection and inflammation of the prostate and urinary tract; nonbacterial prostatitis is an inflamed prostate without bacterial infection; and prostatodynia, sometimes called chronic pelvic pain syndrome (CPPS), is the occurrence of prostatitis symptoms, without inflammation or bacterial infection.

Prostatic intraepithelial neoplasia (PIN) has been identified as a precursor lesion to prostatic carcinoma. PIN refers to the precancerous end of a morphologic spectrum involving cellular proliferation within prostatic ducts, ductules, and acini. Bostwick and Brawer introduced the term PIN in 1987. At an international conference in 1989, the term PIN replaced a variety of terms (e.g. intraductal hyperplasia, hyperplasia with malignant change, large acinar atypical hyperplasia, marked atypia, ductal-acinar dysplasia). The frequency of PIN in men with prostate cancer is significantly higher than in those without cancer. PIN appears to precede cancer by more than 10 years, with a parallel age-related increase in the frequency of PIN and cancer. PIN has been found in 9% of men in the second decade of life, 22% of men in the third decade, and 40% of men in the fourth decade. By the time men reach age 80 years old, the prevalence of PIN is 70%.

Symptoms of the above prostate disorders are similar. Common symptoms are urinary and include dribbling after voiding; feeling that the bladder has not emptied completely after urination; frequent urination, particularly at night (i.e., nocturia); hesitant, interrupted, or weak urine stream caused by decreased force; leakage of urine (i.e., overflow incontinence); pushing or straining to begin urination; recurrent, sudden, urgent need to urinate; and blood in the urine (i.e., hematuria) caused by straining to void.

There are two main classes of drugs that are prescribed for treating prostate disorders: alpha-blockers and 5-alpha-reductase inhibitors.

Alpha-blockers relax the smooth muscles of the arteries, the prostate, and the bladder neck. Relaxing the smooth muscles around the bladder neck helps relieve urinary obstruction. While alpha-blockers help alleviate some of the symptoms, this drug does not cure BPH. There are several different alpha-blockers. Currently, these are alfuzosin (Xatral), doxazosin (Cardura), indoramin (Doralese), prazosin (Hypovase), terazosin (Hytrin BPH), and tamsulosin (Flomax MR). Side effects can include headaches, dizziness, low blood pressure, fatigue, weakness, and difficulty breathing. Long-term risks and benefits have not been studied.

5-Alpha-reductase inhibitors inhibit the production of the enzyme that converts testosterone to DHT. Thus, 5-alpha-reductase inhibitors are able to reverse BPH to some extent and shrink the prostate. Side effects include reduced libido, impotence, problems with ejaculation, breast tenderness and enlargement, and reduced sperm count. Long-term risks and benefits have not been studied. Safety of 5 alpha reductase inhibitors is a concern for pregnant women who may be exposed to broken capsules, and patients on this medication should stop for 6 months before donating blood.

Surgery is also an option for relief of symptoms of BPH and prostatitis and is recommended for patients who experience serious complications, and has the most complications including urinary incontinence, overactive bladder and a possible worsening of urinary symptoms as well as impotence, retrograde ejaculation (dry climax), and possibly sterility. Prostatectomy complications include incontinence and impotence.

Natural therapies may be used to treat prostate disorders. Saw palmetto (i.e. *Serenoa repens*) acts as a 5-alpha-reductase inhibitor reducing the production of DHT and also preventing DHT from binding to the prostate. Schneider et al., Fortschr. Med. 113: 37-40 (1995); Kock and Biber, Urologe 334: 90-95 (1994). Side effects include mild digestive distress as well as some of the side effects associated with the 5-alpha-reductase inhibiting drug medications, such as mild pruritis, headache, hypertension, erectile dysfunction, ejaculatory disorders, and decreased libido. Pygeum (*Pygeum africanum*) contains three compounds that may help the prostate: pentacyclic triterpenoids, which have a diuretic action; phytosterols, which have anti-inflammatory activity; and ferulic esters, which help rid the prostate of any cholesterol deposits that accompany BPH. Andro and Riffaud, Curr. Ther. Res. 56: 796-817 (1995). Stinging nettles (*Urtica dioica*) can also reduce BPH symptoms and may increase urinary volume and the maximum flow rate of urine in men with early-stage BPH. Kock and Biber, Urologe 334:90-95 (1994). Side effects include digestive distress.

All of the mentioned treatment options for prostate disorders have some associated side effects. Pharmaceutical drug and herbal treatment options commonly do not completely resolve symptoms of urinary incontinence and overactive bladder that may be associated with the disorders. The bladder and urethra are significantly impacted by BPH, contributing to long term weakness in this area and resultant impaired bladder tone and function.

There is currently a need for new compositions for the prevention and treatment of prostate disorders with emphasis not just on the prostate but also on the bladder and its associated symptoms, including overactive bladder (OAB), nocturia, poor urinary stream and urinary incontinence (UI). There is a need for these new compositions without many of the unwanted side effects. There is also a need for these improvements in prostate and bladder symptoms to occur within a shorter time frame of weeks rather than many months.

SUMMARY

One embodiment described herein is related to herbal compositions for the prevention or treatment of disorders of the prostate, for example, enlarged prostate or benign prostatic hyperplasia (hereinafter, "BPH"), prostatitis, prostatic intraepithelial neoplasia, and the symptoms of BPH, including overactive bladder (OAB), nocturia, poor urinary stream and urinary incontinence (UI) and straining to urinate. The herb-containing compositions provide herein can be formulated in a dry delivery system, liquid delivery system, or a controlled-release vehicle. In one embodiment, the herb-containing compositions are formulated as oral dosage units which include a tablet; dry powder; capsule; and caplet.

One embodiment provides an herb-containing composition, comprising (i) a *Crateva nurvala* extract preparation; (ii) an *Equisetum arvense* extract preparation; (iii) a *Lindera aggregata* extract preparation; and (iv) a *Serenoa repens* extract preparation; wherein the herb-containing composition is formulated as an oral dosage unit.

An alternative embodiment provides an herb-containing composition, comprising: (i) a *Crateva nurvala* extract preparation present; (ii) an *Equisetum arvense* extract preparation; (iii) a *Lindera* aggregata extract preparation; and (iv) a *Serenoa repens* extract preparation; wherein the herb-containing composition is formulated as an oral dosage unit, and wherein the *Equisetum arvense* stem extract preparation and the *Lindera aggregata* root extract preparation are present at the same concentration.

An effective daily amount of each herb ranges from about 1 g to 18 g *Crateva nurvala*, about 750 mg to 12 g *Equisetum arvense*, about 750 mg to 12 g *Lindera aggregata*, and about 1 g to 18 g *Serenoa repens*. In an alternative embodiment, an effective daily amount of each herb ranges from about 3 g to 12 g *Crateva nurvala*, about 1.5 g to 6 g *Equisetum arvense*, about 1.5 g to 6 g *Lindera aggregata*, and about 2 g to 12 g *Serenoa repens*. In another alternative embodiment, an effective daily amount of each herb ranges from about 4 g to 8 g *Crateva* nurvala, about 2 g to 4 g *Equisetum arvense*, about 2 g to 4 g *Lindera aggregata*, and about 3 g to 8 g *Serenoa repens*. In another alternative embodiment, an effective daily amount of each herb contains about 6 g *Crateva nurvala*, about 3 g *Equisetum arvense*, about 3 g *Lindera aggregata*, and about 6 g *Serenoa repens*.

In an alternative embodiment, the effective daily amount is taken in two equivalent doses. For example, in one embodiment, each doses contains about 3 g *Crateva nurvala*, about 1.5 g *Equisetum arvense*, about 1.5 g *Lindera aggregata*, and about 3 g *Serenoa repens*.

In another alternative embodiment, the effective daily amount is taken in three equivalent doses. For example, in one embodiment, each dose contains about 2 g *Crateva nurvala*, about 1 g *Equisetum arvense*, about 1 g *Lindera aggregata*, and about 3.2 g *Serenoa repens*.

An alternative embodiment provides an herb-containing composition with at least one of the herbal components as a standardized preparation. In an alternative embodiment, the herb-containing composition has two of the herbal components as standardized preparations. In another embodiment, the herb-containing composition has three of the herbal components as standardized preparations. In another embodiment, all four herbal components of the herb-containing composition (*Crateva nurvala*, *Equisetum arvense*, *Lindera aggregata*, and *Serenoa repens*) are standardized preparations.

An alternative embodiment provides a kit for the prevention or treatment of the symptoms of urinary incontinence or overactive bladder comprising *Crateva nurvala*, *Equisetum arvense*, *Lindera aggregata*, and *Serenoa repens*, each separately in the form of a tablet. In an alternative embodiment, two, three, or four herbs are combined in a single tablet. In an alternative embodiment, the kit comprises sufficient tablets for the prevention or treatment of the symptoms of BPH in a subject for 30 days. In alternative embodiments, the kit comprises sufficient tablets for the prevention or treatment of the symptoms of BPH in a subject for 7, 14, 21, or 28 days. In another alternative embodiments, the kit comprises a sufficient number of tablets for the prevention or treatment of the symptoms of BPH in a subject for 2, 3, 4, 5, 6, 9, or 12 months.

Another embodiment provides a method for the prevention or treatment of the symptoms of BPH. The method comprises administering an herb-containing composition to a subject in need thereof, the herb-containing composition comprising: (i) a *Crateva nurvala* stem/bark extract preparation; (ii) an *Equisetum arvense* stem extract preparation; (iii) a *Lindera aggregata* root extract preparation; and (iv) a *Serenoa repens* leaf/berry extract preparation; wherein the herb-containing composition is formulated as an oral dosage unit.

BRIEF DESCRIPTION OF THE DRAWINGS

The invention will be more fully understood by reference to the following drawings, which are for illustrative purposes only.

DETAILED DESCRIPTION

Figure 1:
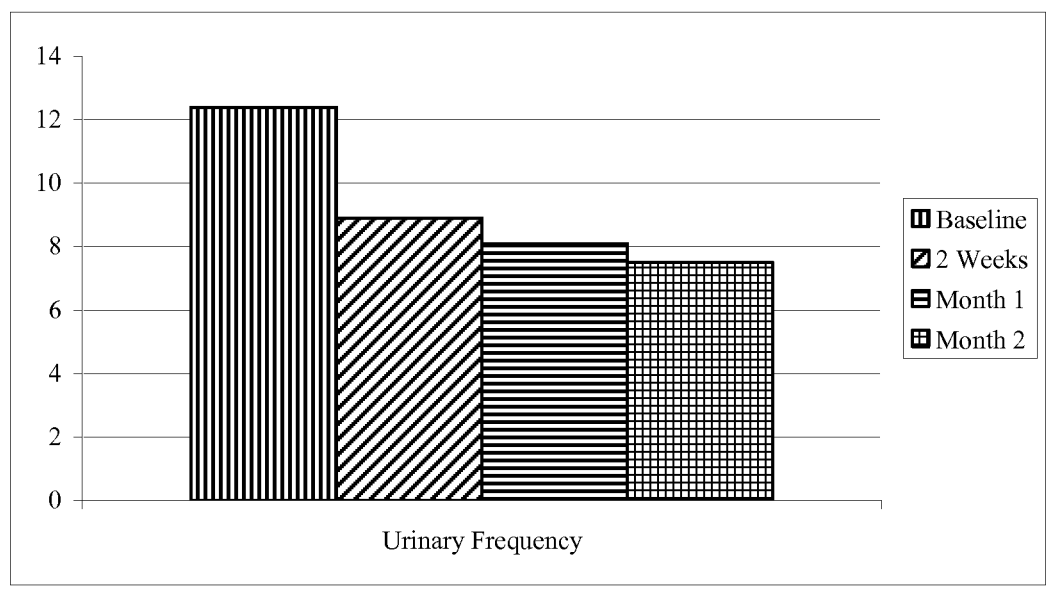
FIG. 1 is a histogram graph showing the Average Urinary Frequency (per day) in a participant population during clinical assessment in one embodiment

It is to be appreciated that certain aspects, modes, embodiments, variations and features of the invention are described below in various levels of detail in order to provide a substantial understanding of the present invention. In general, such disclosure provides beneficial herb-containing compositions, combinations of such compositions with other dietary supplement compositions, and related methods of producing and using the same.

Accordingly, the various aspects of the present invention relate to therapeutic or prophylactic uses of certain particular herb-based compositions in order to prevent or treat a disease, injury or condition related to BPH. Accordingly, various particular embodiments that illustrate these aspects follow.

It is to be appreciated that the various modes of treatment or prevention of medical conditions as described are intended to mean "substantial", which includes total but also less than total treatment or prevention, and wherein some biologically or medically relevant result is achieved.

A "subject" as described in some embodiments herein can be a mammal, such as a human, but can also be an animal, such as domestic animals (e.g., dogs, cats and the like), farm animals (e.g., cows, sheep, pigs, horses and the like), and laboratory animals (e.g., rats, mice, guinea pigs and the like).

An "effective amount" of a composition as described in some embodiments herein can be a quantity sufficient to achieve a desired therapeutic and/or prophylactic effect, for example, an amount which results in the prevention of, or a decrease in the symptoms associated with, a disease that is being treated. The amount of composition administered to the subject, particularly one in need of the composition, can depend on the type and severity of the disease and on the characteristics of the individual, such as general health, age, sex, body weight and tolerance to drugs. It can also depend on the degree, severity and type of disease. A skilled artisan will be able to determine appropriate dosages depending on these and other factors. Typically, an effective amount of the compositions described herein can be sufficient for achieving a therapeutic or prophylactic effect.

In some embodiments, it can be advantageous to formulate oral compositions in a dosage unit form for ease of administration and uniformity of dosage. Dosage unit forms described in some embodiments can refer to physically discrete units suited as unitary dosages for the subject to be treated; each unit containing a predetermined quantity of active composition calculated to produce the desired therapeutic effect in association with the suitable pharmaceutical carrier. The specification for the dosage unit forms provided in one embodiment may be dictated by and directly dependent on the characteristics of the dietary supplement and the particular therapeutic effect to be achieved, and the limitations inherent in the art of producing such an active composition for the treatment of individuals. The pharmaceutical compositions can be included in a container, pack, or dispenser, together with instructions for administration. Generally, in some embodiments an oral dose is taken two-times to four-times daily, until symptom relief is apparent. The compositions provided herein can also be administered in combination with each other, or with one or more additional therapeutic compositions.

Herbal Ingredients

*Crateva nurvala* (or "*C. nurvala*") is a moderate-sized tree attaining a height of over 15 meters; it is named after cratevas (Krateuas), a Greek naturalist and physician of the first Century B.C. Common throughout India, the much-branched tree with a head of glossy trifoliate leaves looks very majestic when in full bloom from March to May (earlier in the South). The bark of the tree is reported to be used as a demulcent, antipyretic, sedative, alternative and tonic.

*Equisetum arvense* (or "*E. arvense*") (botanical synonyms and common names include, for example, Horsetail; Shavegrass; Bottle-brush; Paddock-pipes; Dutch Rushes; Pewterwort; Shavegrass; Pewterwort; Bottlebrush; Horsetail rush; Paddock-pipes; Dutch rushes; Mare's tail) is a European herb that grows in moist waste places throughout temperate regions of the world and is cultivated in Yugoslavia. This perennial plant is common to moist loamy or sandy soil all over North America and Eurasia. Compared to the other herbs in the plant kingdom, horsetail is very rich in silicon. *Equisetum* is used medicinally. The sterile stems are harvested in summer and dried. The barren stems are useful as medicine, appearing after the fruiting stems have died down, and are used in their entirety, cut off just above the root. The herb is used either fresh or dried, but can be most efficacious when fresh in one embodiment. A fluid extract is prepared from it. The ashes of the plant are also employed.

*Lindera aggregata* (or "*L. aggregata*") (botanical synonyms and common names include *Lindera strychnifolia*, Japanese evergreen spicebush, Chinese allspice, Evergreen *Lindera*, Kosterm, Uyaku (Japanese), Oyak (Korean)) is a Chinese herb grown in locations including Zhejiang, Hunan, Anhui, Guangdong, and Guangxi. (Bensky and Gamble). *Lindera* is an evergreen Shrub growing to 9 m (29 ft 6 in). The flowers are dioecious (i.e., individual flowers are either male or female, but only one sex is to be found on any one plant so both male and female plants must be grown if seed is needed). The plant is not self-fertile. The plant tends to prefer light (sandy), medium (loamy) and heavy (clay) soils, preferring moist soil. The plant tends to prefer acid and neutral soils and can grow in very acid soils and in semi-shade (light woodland). It can be harvested in winter or spring (Bensky and Gamble). The root and leaves are used therapeutically.

*Serenoa repens* (botanical synonyms and common names include *Serenoa serrulata, Sabal serrulata, Sabal, Sabal fructus*, Zwegpalme, and saw palmetto (Mills and Bone, 2000). Saw palmetto is a member of the Palmae (palm) family and is native to the southern eastern area of North America. The leaves are palmate, without a continuing rib and are divided into lance-shaped linear-lanceolate leaflets.

The petiole has a sharp spiny edge that can cut clothing or legs, hence the name "saw" and the palmetto is derived from the plants palm-like appearance. The fruit, a one-seeded, dark brown, olive-like mesocarp drupe, also known as the berry, is used medicinally. Liposterolic extracts are commonly used therapeutically; however, extracts and tinctures are also documented as having therapeutic benefits.

Herbs are useful in various forms, for example, as a homogenized mixture obtained by grinding or chopping an herb. The herbs are optionally subjected to processing such as extractions, for example by obtaining a filtrate by filtering or a supernatant by centrifugation. Known methods are readily used to extract a leaf, root, seed, stem, bark etc as appropriate. In certain embodiments, extracts that contain purified active ingredients are prepared. An isolated active ingredient is an ingredient purified from C. nurvala, E. arvense, L. aggregata, or S. repens, that has activity to control (i.e., typically reduce) the symptoms of BPH in a subject. Administration or use of an isolated active ingredient of another herb of the compositions herein, is considered to be a use or administration of the herb itself. The inventor has identified certain compounds in the herbs above without wishing to be bound by theory about compounds and metabolites in the herbs and mechanisms of how the herbs in the compositions herein control the symptoms of BPH.

In one embodiment, the C. nurvala herb preparation can be extracted from the stem and/or bark of the plant, and the preparation is present at a concentration at least about 3,000 mg dry weight equivalents per oral dosage unit. That is, the starting material is 3,000 mg of C. nurvala dry stem/bark. This starting material is eventually concentrated during the manufacturing process to a ratio ("extract ratio") of at least about 10 (i.e., 10:1), such as at least about 20, such as at least about 25, such as at least about 30, such as at least about 35, such as at least about 40. In one embodiment, the ratio is between about 25 and about 35. As an illustrative example, a ratio of 10 would be equivalent to 300 mg of C. nurvala preparation. Accordingly, 300 mg of C. nurvala stem/bark preparation (which is concentrated) is equivalent to 3,000 mg dry weight of C. nurvala stem/bark or 3,000 mg of C. nurvala dry stem/bark starting material. In one embodiment, the C. nurvala herb preparation is derived from the stem and/or bark parts of the C. nurvala herb, i.e., a C. nurvala stem/bark extract preparation.

The E. arvense herb preparation can be extracted from the stem of the plant, and the preparation is present at a concentration of at least about 1,500 mg dry weight equivalents per oral dosage unit. That is, the starting material is 1,500 mg of E. arvense herb. This starting material is eventually concentrated during the manufacturing process to an extract ratio of at least about 5, such as at least about 8, such as at least about 10, such as at least about 15. As an illustrative example, a ratio of 4 or 5 would be equivalent to 375 mg or 300 mg, respectively, of E. arvense herb preparation. Thus, in the case of a concentration ratio of 5, for example, 300 mg of E. arvense herb preparation (which is concentrated) is equivalent to 1,500 mg dry weight of E. arvense herb or 1,500 mg of E. arvense dry herb starting material. In one embodiment, the E. arvense herb preparation is derived from the stem parts of the E. arvense herb, i.e., a E. arvense stem extract preparation.

The L. aggregata herb preparation can be extracted from the stem of the plant, and the preparation is present at a concentration of at least about 1,500 mg dry weight equivalents per oral dosage unit. That is, the starting material is 1,500 mg of L. aggregata herb. This starting material is eventually concentrated during the manufacturing process to an extract ratio of at least about 5, such as at least about 8, such as at least about 10, such as at least about 15. As an illustrative example, a ratio of 4 or 5 would be equivalent to 375 mg or 300 mg, respectively, of L. aggregata herb preparation. Thus, in the case of a concentration ratio of 5, for example, 300 mg of L. aggregata herb preparation (which is concentrated) is equivalent to 1,500 mg dry weight of L. aggregata herb or 1,500 mg of L. aggregata dry herb starting material. In one embodiment, the L. aggregata herb preparation is derived from the root parts of the L. aggregata herb, i.e., a L. aggregata root extract preparation.

In one embodiment, the S. repens herb preparation can be extracted from the leaf and/or berry of the plant, and the preparation is present at a concentration at least about 3,200 mg of S. repens dry leaves and/or berries. This starting material is eventually concentrated during the manufacturing process to an extract ratio of at least about 5, such as at least about 8, such as at least about 10, such as at least about 15. As an illustrative example, a ratio of 10 would be equivalent to 320 mg of the S. repens herb preparation. Thus, in the case of a concentration ratio of 5, for example, 640 mg of S. repens herb preparation (which is concentrated) is equivalent to 3,200 mg dry weight of S. repens herb or 3,200 mg of S. repens dry herb starting material. In one embodiment, the S. repens herb preparation is derived from the leaf and/or berry parts of the S. repens herb, i.e., a S. repens leaf and/or berry extract preparation.

In one embodiment, any of the herb preparations, including the C. nurvala, E. arvense, L. aggregata, and S. repens herb preparations, can be extracted using alcohol (e.g., 45-95% ethanol). In another embodiment, the S. repens herb preparation can be extracted using carbon dioxide ($CO_2$). In another embodiment, the S. repens herb preparation can be extracted using a super-critical fluid extraction (SFE) method of separating one component (the extract) from another (the matrix) using super-critical fluids as the extracting solvent. Extraction is usually from a solid matrix, but can also be from liquids. Carbon dioxide ($CO_2$) is commonly used as the super-critical fluid, sometimes modified with co-solvents such as ethanol or methanol. Extraction conditions for super-critical $CO_2$ may be above the critical temperature of 31° C. and critical pressure of 74 bar.

In some embodiments, the herbal ingredients described herein, alone or in combination, can provide the following remedy or support:

Bladder and Tone Control

The herbs Crateva, Horsetail, and Lindera, are traditionally recommended in herbal medicine for both BPH and symptoms of bladder weakness such as frequency, urgency and bladder accidents.[1,2,3,4] Clinical research using Crateva has shown it acts as a bladder tonic in men, decreases residual urine volume and allows for more complete bladder emptying.[1] It has tonic effects on the bladder and is recommended for poor bladder tone and symptoms of incontinence.

Clinical research has shown the effectiveness Crateva and Horsetail in addressing bladder symptoms in men with BPH such as nocturia, increased frequency, overactive bladder and difficulty voiding, as well as improving quality of life for those affected.[5]

Crateva has beneficial effects on neurogenic bladder and post-prostatectomic atony of the bladder.[1] Crateva is shown to produce a significant reduction in retention of urine in men with hypotonic bladder as a result of benign prostatic hypertrophy. Crateva acts to increase the tone of the bladder and the expulsive force of urine, thereby helping effective evacuation.[1] Crateva normalizes the tone of the urinary bladder and significantly decreases residual urine volume.

Research also supports the effectiveness of the combined Crateva and Horsetail for bladder control.[5,6] A pilot study using this combination showed improvements in bladder frequency, leakage, urgency and bladder pain or discomfort.[6] A larger scale placebo-controlled trial also shows this combination improves bladder symptoms of incontinence, frequency, nocturia, urgency and bladder discomfort, with over 79% participants experiencing improvement.[5]

Prostate Support

Saw palmetto (Serenoa serrulata) is documented as providing relief from BPH symptoms. Saw palmetto acts as a 5 alpha reductase inhibitor therefore lowering DHT and is an antioestrogenic agent.[8] Experimental evidence also suggests Saw palmetto extract blocks the binding of DHT to prostate cells. It does not appear to have the level of side effects that are associated with 5 alpha reductase inhibiting drugs. The fatty acids and sterols in Saw palmetto, including oleic acid, lauric acid, campasterol, stigmasterol, beta-sitosterol and others, are believed to be responsible for these actions.[7-9]

Clinical studies conducted over the last fifteen years suggest Saw palmetto extract can exert effective activity in the maintenance and support of prostate health. Saw palmetto extract has been reported to improve urinary functions and prostate function. Quality of life scores have also improved. The results with Saw palmetto extract have been duplicated in open trials and controlled, double-blind studies.[7-14]

Renal Protection

*Crateva* and *Lindera* are also shown to have kidney protective effects; *Crateva* has been shown to be nephroprotective in rat's exposed to toxic doses of cadmium, while *Lindera* preserves renal function in animals with diabetic nephropathy.[15, 16]

Reduce Inflammation

*Crateva* and *Lindera* have anti-inflammatory and antibacterial properties.[17-20] They help to inhibit acute, sub-acute and chronic inflammations and are beneficial with Saw palmetto for pro statitis.[10-14]

Antioxidant Protection

*Lindera* has potent antioxidant effects to preserve tissue and function of the genito-urinary system. *Lindera*, Selenium and lycopene (derived from tomato, *Lycopersicon esulentum*) prevent disease of the prostate and are beneficial in cases of BPH.

The human prostate contains a high concentration of zinc, which is known to be a key mineral for prostate health. Zinc acts as a 5 alpha reductase inhibitor and is considered to play an important role in the etiology of BPH.[22, 23]

Prostate Protection

Vitamin D absorption and production decreases with age. Vitamin D appears to be actively metabolized in the prostate and Vitamin D influences androgen receptors. Research suggests that vitamin D deficiency may increase the initiation and progression of prostate cancer.[26 27]

Kidney/Bladder Stones

*Crateva* and Horsetail balance urinary minerals and reduce the likelihood of stone formation.[29,30] A key constituent of *Crateva*, lupeol, has been shown in a number of studies to have anti-oxaluric and anti-calcuric effects leading to increased spontaneous passing of these two most common forms of stones as well as symptomatic relief.[29,31,32] Horsetail constituents inhibit xanthine oxidase and subsequent urate calculi formation.[34] It is thought that this effect is promoted by a tonic contractile effect of *Crateva* and Horsetail on the smooth muscle, which also assists with bladder control.[1,29,31]

Incontinence/Over Active Bladder (OAB)

*Crateva* and Horsetail help to improve the tone of the bladder wall. *Crateva* has beneficial effects on neurogenic bladder and post-prostatectomic atony of the bladder.[1] *Crateva* is shown to produce a significant reduction in urinary symptoms of frequency, incontinence, pain and retention of urine in men with hypotonic bladder as a result of benign prostatic hypertrophy. *Crateva* acts to increase the tone of the bladder and the expulsive force of urine, thereby helping effective evacuation.[1] *Crateva* normalizes the tone of the urinary bladder and significantly decreases residual urine volume.

Animal studies support this. *Crateva* has been shown to increase the tone of both smooth and skeletal muscle in vitro.[33] Forty days of treatment produced dramatic improvement.

Research also supports the effectiveness of the combined *Crateva* and Horsetail for bladder control.[5,6] This combination showed improvements in bladder emptying frequency, leakage, urgency and bladder pain or discomfort with best results occurring after two to three months of treatment.[5,6]

*Lindera* has a long history of use in Traditional Chinese Medicine for kidney and bladder health and is specific for frequent urination and loss of bladder control.[4,40] *Lindera* is also recommended for the treatment of renal disease.[4]

Quality of Life

Poor bladder control is shown to negatively affect emotional health and to reduce quality of life for the sufferer.[35,36] Research has shown the *Crateva* and Horsetail combined significantly improved quality of life measurements including feeling less frustration, increased social activities, and better travel.[5,6]

Anti-Inflammation

All of three herbs, *Crateva, Lindera* and Horsetail, show anti-inflammatory effects.[17-20,37-39] *Crateva* and *Lindera* have anti-inflammatory and antibacterial properties.[17-20,37-39] The positive effect on chronic urinary tract infections is most likely a combination of anti-bacterial and anti-inflammatory actions.

Kidney Protection

*Crateva* and *Lindera* are also shown to have kidney protective effects; *Crateva* has been shown to be nephroprotective in rats exposed to toxic doses of cadmium, while *Lindera* preserves renal function in animals with diabetic nephropathy.[15,16]

Animal research demonstrates that *Lindera* slows the progression of diabetic nephropathy (destruction of the kidneys that can occur as a complication of diabetes) and could therefore be used as a preventative approach to protect renal function from deterioration.[16] Use of *Lindera* can result in improved renal function, as evaluated by creatinine clearance and serum creatinine Kidneys of the *Lindera* treated group showed glomeruli with greater area and cell population.

Anti-Oxidant/Anti-Aging

More recent research has shown that *Lindera* has potent antioxidant effects to preserve tissue and function of urinary system. It has potent antioxidant scavenging activity against ROS and RNS (reactive oxygen species and reactive nitrogen species—both common oxidants that damage body tissues) that effectively inhibits lipid peroxidation.[41] *Lindera* extracts show protection against neuronal oxidative injury and may be of benefit to protect against neuronal Central nervous system degeneration.[42] *Lindera* also has antibacterial effects.[4]

Joint Support

*Lindera* is also used traditionally for rheumatic complaints, and multiple studies have shown that *Lindera* or *Lindera* extracts reduce inflammation.[19,20,38] Alkaloids derived from *Lindera* have been shown in animal studies to have anti-inflammatory effects and to be of benefit for rheumatoid arthritis (RA).[38] *Lindera* has also been shown to inhibit the effects of inflammatory mediators from macrophages. These help illustrate therapeutic efficiency on the inflammation and joint destruction in RA.[19] This supports the use of *Lindera* for analgesic and anti-inflammatory actions to improve symptoms of RA and protect joints from destruction.[20]

Cardiovascular Support

Lindera is traditionally recommended for the treatment of cardiac support. Animal studies have shown that Lindera can improve heart function.[40]

Herb-Containing Compositions

One embodiment described herein provides herb-containing compositions useful in a method of prophylaxis or treatment of disorders of BPH—e.g., urinary incontinence, enuresis (e.g., bed-wetting), benign prostatic hyperplasia, urinary calculi, cystitis, and urinary tract infection (or "UTI"). In particular, one embodiment provides a composition, which contains C. nurvala, E. arvense, L. aggregata and S. repens; in one embodiment the composition is useful in the prevention and treatment of disorders of BPH. In one embodiment, the herb-containing composition contains C. nurvala extract preparation, E. arvense extract preparation, L. aggregata extract preparation, and S. repens extract preparation.

In one embodiment, the herb-containing composition is an oral supplement included in a dry delivery system, e.g., tablet, dry powder, and dry meal replacement mixture. In another embodiment, the herb-containing composition is an oral supplement included in a liquid delivery system, e.g., capsule, caplet, or beverage. In another embodiment, the herb-containing composition is an oral supplement included in a controlled-release vehicle, e.g., tablet, caplet, and capsule.

In one embodiment, the herb-containing composition contains from about 1,000 mg to about 6,000 mg dry weight equivalents C. nurvala stem/bark extract per oral dosage unit. In another embodiment, the herb-containing composition contains from about 1,000 mg to about 4,000 mg dry weight equivalents C. nurvala stem/bark extract per oral dosage unit. In another embodiment, the herb-containing composition contains from about 2,500 mg to about 3,500 mg dry weight equivalents C. nurvala stem/bark extract per oral dosage unit. In one embodiment, the herb-containing composition contains about 3,000 mg dry weight equivalents C. nurvala stem/bark extract per oral dosage unit. A C. nurvala stem/bark extract is an extract prepared using both the stem parts and bark of the C. nurvala herb.

In another embodiment, the herb-containing composition contains from about 1,000 mg to about 6,000 mg dry weight equivalents C. nurvala stem extract per oral dosage unit. In another embodiment, the herb-containing composition contains from about 1,000 mg to about 4,000 mg dry weight equivalents C. nurvala stem extract per oral dosage unit. In another embodiment, the herb-containing composition contains from about 2,500 mg to about 3,500 mg dry weight equivalents C. nurvala stem extract per oral dosage unit. In one embodiment, the herb-containing composition contains about 3,000 mg dry weight equivalents C. nurvala stem extract per oral dosage unit.

In another embodiment, the herb-containing composition contains from about 1,000 mg to about 6,000 mg dry weight equivalents C. nurvala bark extract per oral dosage unit. In another embodiment, the herb-containing composition contains from about 1,000 mg to about 4,000 mg dry weight equivalents C. nurvala bark extract per oral dosage unit. In one embodiment, the herb-containing composition contains from about 2,500 mg to about 3,500 mg dry weight equivalents C. nurvala bark extract per oral dosage unit. In one embodiment, the herb-containing composition contains about 3,000 mg dry weight equivalents C. nurvala bark extract per oral dosage unit.

In one embodiment, to prepare the herb-containing composition, the bark and/or stems of C. nurvala are isolated from the rest the C. nurvala plant and dried. The dried bark and stems of C. nurvala are extracted using 70% ethanol/water. The liquid extract is then concentrated to a ratio of 10:1. Maltodextrin is used as an excipient. The final product, i.e., C. nurvala stem/bark extract, used in the herb-containing composition is a brown to dark brown powder. In an alternative embodiment, the liquid extract is then concentrated to a ratio of between about 25 and 35. Maltodextrin is used as an excipient.

In one embodiment, the E. arvense herb preparation component of the herb-containing composition is derived from the leaf of the E. arvense herb. In one embodiment, the E. arvense herb preparation component of the herb-containing composition is derived from the stem of the E. arvense herb. In another embodiment, the E. arvense herb preparation component of the herb-containing composition is derived from a mixture of plant parts of the E. arvense herb. In another embodiment, the E. arvense herb preparation component of the herb-containing composition is derived from all the parts of the plant that extend above-ground. In one embodiment, the herb-containing composition contains from about 1 mg to about 3,000 mg dry weight equivalents E. arvense herb preparation per oral dosage unit. In another embodiment, the herb-containing composition contains from about 500 mg to about 2,500 mg dry weight equivalents E. arvense herb preparation per oral dosage unit. In another embodiment, the herb-containing composition contains from about 1,000 mg to about 2,000 mg dry weight equivalents E. arvense herb preparation per oral dosage unit. In another embodiment, the herb-containing composition contains from about 1,300 mg to about 1,600 mg dry weight equivalents E. arvense herb preparation per oral dosage unit. In one embodiment, the herb-containing composition contains about 1,500 mg dry weight equivalents E. arvense stem extract per oral dosage unit.

In one embodiment, the L. aggregata herb preparation component of the herb-containing composition is derived from the roots of the L. aggregata herb. In one embodiment, the L. aggregata herb preparation component of the herb-containing composition is derived from the leaf and/or stem of the L. aggregata herb. In another embodiment, the L. aggregata herb preparation component of the herb-containing composition is derived from a mixture of plant parts of the L. aggregata herb. In another embodiment, the L. aggregata herb preparation component of the herb-containing composition is derived from all the parts of the plant that extend above-ground and/or below-ground. In one embodiment, the herb-containing composition contains from about 1 mg to about 3,000 mg dry weight equivalents L. aggregata herb preparation per oral dosage unit. In another embodiment, the herb-containing composition contains from about 500 mg to about 2,500 mg dry weight equivalents L. aggregata herb preparation per oral dosage unit. In another embodiment, the herb-containing composition contains from about 1,000 mg to about 2,000 mg dry weight equivalents L. aggregata herb preparation per oral dosage unit. In another embodiment, the herb-containing composition contains from about 1,300 mg to about 1,600 mg dry weight equivalents L. aggregata herb preparation per oral dosage unit. In some embodiments, the L. aggregata herb preparation can be present at a comparable, such as the same, concentration as the E. arvense preparation. In one embodiment, the herb-containing composition contains about 1,500 mg dry weight equivalents L. aggregata root extract per oral dosage unit.

In one embodiment, the herb-containing composition contains from about 1,000 mg to about 6,000 mg dry weight equivalents *S. repens* leaf/berry extract per oral dosage unit. In another embodiment, the herb-containing composition contains from about 1,000 mg to about 4,000 mg dry weight equivalents *S. repens* leaf/berry extract per oral dosage unit. In another embodiment, the herb-containing composition contains from about 2,500 mg to about 3,500 mg dry weight equivalents *S. repens* leaf/berry extract per oral dosage unit. In one embodiment, the herb-containing composition contains about 3,200 mg dry weight equivalents *S. repens* leaf/berry extract per oral dosage unit. A *S. repens* leaf/berry extract is an extract prepared using both the leaves and berries of the *S. repens* herb.

In another embodiment, the herb-containing composition contains from about 1,000 mg to about 6,000 mg dry weight equivalents *S. repens* leaf extract per oral dosage unit. In another embodiment, the herb-containing composition contains from about 1,000 mg to about 4,000 mg dry weight equivalents *S. repens* leaf extract per oral dosage unit. In another embodiment, the herb-containing composition contains from about 2,500 mg to about 3,500 mg dry weight equivalents *S. repens* leaf extract per oral dosage unit. In one embodiment, the herb-containing composition contains about 3,200 mg dry weight equivalents *S. repens* leaf extract per oral dosage unit.

In another embodiment, the herb-containing composition contains from about 1,000 mg to about 6,000 mg dry weight equivalents *S. repens* berry extract per oral dosage unit. In another embodiment, the herb-containing composition contains from about 1,000 mg to about 4,000 mg dry weight equivalents *S. repens* berry extract per oral dosage unit. In one embodiment, the herb-containing composition contains from about 2,500 mg to about 3,500 mg dry weight equivalents *S. repens* berry extract per oral dosage unit. In one embodiment, the herb-containing composition contains about 3,200 mg dry weight equivalents *S. repens* berry extract per oral dosage unit.

In one embodiment, to prepare the herb-containing composition, the leaves and/or berries of *S. repens* are isolated from the rest the *S. repens* plant and dried. The dried leaves and berries of *S. repens* can be extracted using 45-90% ethanol/water or using $CO_2$. The liquid extract is then concentrated to a ratio of about 10:1. Maltodextrin may be used as an excipient. The final product, i.e., *S. repens* leaf/berry extract, used in the herb-containing composition is a brown to dark brown powder. In an alternative embodiment, the liquid extract is then concentrated to a ratio of between about 5:1 and about 20:1. In an alternative embodiment, the liquid extract is then concentrated to a ratio of between about 5:1 and about 15:1. In an alternative embodiment, the liquid extract is then concentrated to a ratio of about 10:1. Maltodextrin may be used as an excipient.

Other embodiments of the herbal composition are presented in Table 1.

TABLE 1

Ranges of effective daily amounts of the herbal composition

| Component | Range A (g/day) | Range B (g/day) | Range C (g/day) |
|---|---|---|---|
| C. nurvala | 1-18 | 3-12 | 4-8 |
| E. arvense | 0.75-12 | 1.5-6 | 2-4 |
| L. aggregata | 0.75-12 | 1.5-6 | 2-4 |
| S. repens | 1-18 | 2-12 | 3-8 |

Standardization

An alternative embodiment provides an herb-containing composition with at least one of the herbal components as a standardized preparation. In an alternative embodiment, the herb-containing composition has two of the herbal components as standardized preparations. In another embodiment, the herb-containing composition has three of the herbal components as standardized preparations. In another embodiment, all four herbal components of the herb-containing composition (*Crateva nurvala*, *Equisetum arvense*, *Lindera aggregata*, and *Serenoa repens*) are standardized preparations. Various embodiments of the standardized preparations are provided in Table 2. For example, in alternative embodiment A, all four herbs are non-standardized, while in embodiment P, all four herbs are standardized.

TABLE 2

Various embodiments of the standardized preparations of the herbal composition

| Embodiment | C. nurvala | E. arvense | L. aggregata | S. repens |
|---|---|---|---|---|
| A | — | — | — | — |
| B | * | — | — | — |
| C | — | * | — | — |
| D | — | — | * | — |
| E | — | — | — | * |
| F | * | * | — | — |
| G | — | * | * | — |
| H | — | — | * | * |
| I | * | — | — | * |
| J | * | — | * | — |
| K | — | * | — | * |
| L | * | * | * | — |
| M | * | * | — | * |
| N | * | — | * | * |
| O | — | * | * | * |
| P | * | * | * | * |

NOTE:
Herbs denoted with an asterisk (*) are standardized; herbs denoted with a dash (—) are non-standardized.

One embodiment provides a pharmaceutical composition comprising the herb-containing composition of any one of embodiments A-P in Table 2 and a pharmaceutically-acceptable carrier.

In some embodiments, it has been determined that batch variation in the silicon content and/or flavonoid content expressed as isoquercetrin of *E. arvense* herb preparations can have negative effects on the biological activity of the composition described herein. This problem has been resolved in some embodiments by providing *E. arvense* herb preparations with optimized, standardized silicon content and/or flavonoid content expressed as isoquercetrin. One embodiment provides an herb-containing composition, comprising a *C. nurvala* preparation, a *L. aggregata* preparation, and a standardized *E. arvense* herb preparation with a silicon content from about 3% to about 13% silicon based on total dry weight of the *E. arvense* preparation, wherein the herb-containing composition is formulated as an oral dosage unit. Accordingly, for 1,500 mg dry weight of *E. arvense* herb or 1,500 mg of *E. arvense* dry herb starting material, which produces 300 mg of *E. arvense* herb preparation (which is concentrated), a silicon content from about 3% to about 13% would represent approximately 9 to 39 mg silicon.

In some instances, silicon is identified as a contributor to the biological activity of *E. arvense* herb. Non-standardized preparations of *E. arvense* herb generally contain silicon from about 1.2% to about 6.9% silicon based on total dry weight of preparation. In one embodiment, it has been determined that batch variation in the silicon content of *E. arvense* herb preparations can have negative effects on the biological activity of the composition described herein. This problem can be resolved in one embodiment by providing an *E. arvense* herb preparation with optimized, standardized silicon content. Accordingly, in one embodiment, the silicon content of the *E. arvense* herb preparation in the herb-containing preparation can be standardized. The use of a standardized preparation *E. arvense* herb can be advantageous because the inter-batch variation of silicon can be reduced, thus the composition described herein can yield more consistent preventative or therapeutic effect. In one embodiment, the *E. arvense* herb preparation is standardized to contain from about 3% silicon to about 13% silicon based on the total dry weight of the *E. arvense* herb preparation. In another embodiment, the *E. arvense* herb preparation is standardized to contain from about 5% silicon to about 10% silicon based on the total dry weight of the *E. arvense* herb preparation. In another embodiment, the *E. arvense* herb preparation is standardized to contain at least about 6% silicon based on the total dry weight of the *E. arvense* herb preparation.

In addition to silicon, *E. arvense* contains about 5 percent of a saponin, designated equisetonin, and several flavone glycosides (i.e., flavonoids) including isoquercetrin, galuteolin, and equisetrin. Isoquercetrin (i.e., isoquercitrin; Quercetin 3-O-β-D-glucopyranoside; 4H-1-Benzopyran-4-one, 2-(3,4-dihydroxy-phenyl)-3-(β-D-glucofuranosyloxy)-5,7-dihydroxy-). Flavonoids, e.g., isoquercetrin, may have important pharmacological properties. Many flavonoids are diuretic, some are antispasmodic, anti-inflammatory, antiseptic and even antitumor. However, the predominant action of the flavonoids as a group is on the vascular system. The flavone glycosides and the saponin likely combine to account for the diuretic action of *E. arvense*.

One embodiment provides an herb-containing composition, comprising: a *C. nurvala* stem/bark preparation present at a concentration at least about 3,000 mg dry weight equivalents per oral dosage unit; an *E. arvense* stem extract preparation at a concentration of at least about 1,500 mg dry weight equivalents per oral dosage unit; a *L. aggregata* root extract preparation at a concentration of at least about 1,500 mg dry weight equivalents per oral dosage unit; and a *S. repens* leaf/berry preparation present at a concentration at least about 3,000 mg dry weight equivalents per oral dosage unit. Optionally, the composition can further comprise a total silicon concentration of at least about 32.5 mg dry weight equivalents per oral dosage unit; a phosphorous concentration of at least about 24.9 mg dry weight equivalents per oral dosage unit; a magnesium concentration of at least about 14.5 mg dry weight equivalents per oral dosage unit; and a calcium concentration of at least about 16.3 mg dry weight equivalents per oral dosage unit.

Another embodiment provides an herb-containing composition, comprising a *C. nurvala* stem/bark preparation, an *E. arvense* stem extract preparation with a total flavonoid content from about 0.01% to about 3% total flavonoids based on the total dry weight of the *E. arvense* preparation, a *L. aggregata* root extract preparation; wherein the total flavonoid content is expressed as isoquercetrin and wherein the herb-containing composition is formulated as an oral dosage unit; and a *S. repens* leaf/berry preparation, wherein the *S. repens* preparation can be standardized to have at least one of the following based on total weight of the *Serenoa repens* extract preparation: (i) about 85% to about 95% fatty acids; (ii) lycopene not less than 750 µg dry weight equivalents per oral dosage unit; (iii) zinc (e.g., citrate) not less than 7 mg dry weight equivalents per oral dosage unit; (iv) selenium (e.g., selenomethionine) not less than 12 µg dry weight equivalents per oral dosage unit; and (v) vitamin D (e.g., cholecalciferol) not less than 5 µg dry weight equivalents per oral dosage unit. In one embodiment, the *E. arvense* herb preparation can be a standardized *E. arvense* stem extract preparation. In one embodiment, the standardized *E. arvense* herb preparation further comprises a total flavonoid content from about 0.1% to about 2.5% total flavonoids based on the total dry weight of the *E. arvense* preparation and expressed as isoquercetrin. In one embodiment, the standardized *E. arvense* herb preparation comprises a total flavonoid content from about 0.5% to about 1.5% total flavonoids based on the total dry weight of the *E. arvense* preparation, wherein the total flavonoid content is expressed as isoquercetrin. In one embodiment, the standardized *E. arvense* herb preparation comprises a total flavonoid content from at least about 0.8% total flavonoids based on the total dry weight of the *E. arvense* preparation, wherein the total flavonoid content is expressed as isoquercetrin.

In one embodiment, the standardized *E. arvense* herb preparation further comprises a total flavonoid content from about 0.01% to about 3% total flavonoids based on the total dry weight of the *E. arvense* preparation, wherein the total flavonoid content is expressed as isoquercetrin. In one embodiment, the standardized *E. arvense* herb preparation further comprises a total flavonoid content from about 0.1% to about 2.5% total flavonoids based on the total dry weight of the *E. arvense* preparation and expressed as isoquercetrin. In one embodiment, the standardized *E. arvense* herb preparation further comprises a total flavonoid content from about 0.5% to about 1.5% total flavonoids based on the total dry weight of the *E. arvense* preparation, wherein the total flavonoid content is expressed as isoquercetrin. In one embodiment, the standardized *E. arvense* herb preparation further comprises a total flavonoid content from at least about 0.8% total flavonoids based on the total dry weight of the *E. arvense* preparation, wherein the total flavonoid content is expressed as isoquercetrin.

In another embodiment, it has been determined that batch variation in the total flavonoid content (expressed as isoquercetrin content) of *E. arvense* herb preparations can have negative effects on the biological activity of the composition described herein. This problem has been resolved in some embodiments by providing an *E. arvense* herb preparation with optimized, standardized total flavonoid content (expressed as isoquercetrin content). Accordingly, in one embodiment, the total flavonoid content (expressed as isoquercetrin content) of the *E. arvense* herb preparation in the herb-containing preparation is standardized. The use of a standardized preparation *E. arvense* herb is advantageous because the inter-batch variation of total flavonoid content (expressed as isoquercetrin content) is reduced, thus the composition provided herein can yield more consistent preventative or therapeutic effect. In one embodiment, the *E. arvense* herb preparation is standardized to contain from about 0.01% flavonoids to about 3% flavonoids based on the total dry weight of the *E. arvense* herb preparation, wherein the total flavonoids are expressed as isoquercetrin equivalents. In another embodiment, the *E. arvense* herb preparation is standardized to contain from about 0.1% flavonoids to about 2.5% flavonoids based on the total dry weight of the *E. arvense* herb preparation, wherein the total flavonoids are expressed as isoquercetrin equivalents. In another embodiment, the *E. arvense* herb preparation is standardized to contain from about 0.5% flavonoids to about 1.5% flavonoids based on the total dry weight of the *E. arvense* herb preparation, wherein the total flavonoids are expressed as isoquercetrin equivalents. In another embodiment, the *E.*

*arvense* herb preparation is standardized to contain at least about 0.8% flavonoids based on the total dry weight of the *E. arvense* herb preparation, wherein the total flavonoids are expressed as isoquercetrin equivalents.

In one embodiment, the *E. arvense* herb preparation is standardized to organic silicon content by a solvent extraction process using raw material with a silicon content that met a minimum silicon content, e.g., 3% silicon. In one embodiment, the *E. arvense* herb preparation of the herb-containing composition is derived from the stems of the *E. arvense* herb and standardized for silica content (i.e., *E. arvense* stem extract preparation). Briefly, stem parts of the *E. arvense* herb are removed from the plant and dried. They are then measured for a minimum of 2.5% silicon content via HPLC analysis before being accepted for the extraction process. An extract was obtained using 65% (v/v) ethanol/water extraction solvent. The extract was concentrated to a ratio of approximately 4:1. The extract is then tested again for minimum 3% silicon content via HPLC. The final extract dry concentrate appeared as a fine brown powder with a characteristic odor and taste.

In another embodiment, the *E. arvense* herb preparation is standardized to organic silicon by a solvent extraction process. Briefly, stem parts of the *E. arvense* herb are removed from the plant and dried. Morphological examination of the starting biomass (this includes both microscopic and macroscopic characteristics) can help facilitate using the correct species (e.g., an authenticated voucher specimen is stored on file for species identification). An extract is obtained using hot water (between about 50° C. and about 100° C.) as a solvent. The extract is concentrated to a ratio of approximately 5:1. The extract is then dried. The extract is tested for a minimum of approximately 3% silicon content via UV-Vis Spectrophotometry (silicon dioxide is used as a reference substance). In one embodiment, if the extract falls outside the desired standards above, it is titrated with a dried extract that had undergone the same process as above. The final extract dry concentrate appear as a yellow-brown colored powder.

In one embodiment, the *E. arvense* herb preparation of the herb-containing composition is derived from the stems of the *E. arvense* herb and standardized for total flavonoid content, i.e., *E. arvense* stem extract preparation.

In another embodiment, the *E. arvense* herb preparation is standardized to flavonoid (expressed as isoquercetrin) content by a solvent extraction process. Briefly, stem parts of the *E. arvense* herb are removed from the plant and dried. They are then identified by TLC. (isoquercetrin is used as reference substance). Morphological examination of the starting biomass (this included both microscopic and macroscopic characteristics) can help facilitate using the correct species (e.g., an authenticated voucher specimen was stored on file for species identification). An extract was obtained using hot water (between about 50° C. and about 100° C.) as a solvent. The extract is concentrated to a ratio of approximately 5:1. The extract is then dried. The extract is tested for a minimum of approximately 0.01% isoquercetrin via UV-Vis Spectrophotometry (isoquercetrin is used as reference substance). If the extract falls outside the desired standards above, it is titrated with a dried extract that had undergone the same process as above. The final extract dry concentrate appears as a yellow-brown colored powder.

In one embodiment, the *E. arvense* herb preparation is standardized to organic silicon content and flavonoid content (expressed as isoquercetrin) using the methods described above.

In certain embodiments, the *Serenoa repens* extract preparation can be standardized, alone, or in addition to the other herbal preparations also being standardized, as described herein. In certain embodiments, the *Serenoa repens* extract preparation can be standardized to have at least one of the following based on total weight of the *Serenoa repens* extract preparation: (i) about 85% to about 95% fatty acids; (ii) lycopene not less than 750 µg dry weight equivalents per oral dosage unit; (iii) zinc (e.g., citrate) not less than 7.5 mg dry weight equivalents per oral dosage unit; (iv) selenium (e.g., selenomethionine) not less than 12 µg dry weight equivalents per oral dosage unit; and (v) vitamin D (e.g., cholecalciferol) not less than 5 µg dry weight equivalents per oral dosage unit.

In one embodiment, the *S. repens* herb preparation is standardized to contain from about 75% to about 99% fatty acids based on the total dry weight of the *S. repens* herb preparation. In another embodiment, the *S. repens* herb preparation is standardized to contain from about 85% to about 95% fatty acids based on the total dry weight of the *S. repens* herb preparation. In another embodiment, the *S. repens* herb preparation is standardized to contain from about 90% fatty acids based on the total dry weight of the *S. repens* herb preparation.

In another embodiment, the *S. repens* herb preparation is standardized to contain lycopene not less than 10 µg dry weight equivalents per oral dosage unit based on the total dry weight of the *S. repens* herb preparation. In another embodiment, the *S. repens* herb preparation is standardized to contain lycopene not less than 500 µg dry weight equivalents per oral dosage unit based on the total dry weight of the *S. repens* herb preparation. In another embodiment, the *S. repens* herb preparation is standardized to contain lycopene not less than 750 µg dry weight equivalents per oral dosage unit based on the total dry weight of the *S. repens* herb preparation. In another embodiment, the *S. repens* herb preparation is standardized to contain lycopene not less than 2,000 µg dry weight equivalents per oral dosage unit based on the total dry weight of the *S. repens* herb preparation.

In another embodiment, the *S. repens* herb preparation is standardized to contain zinc (e.g., citrate) not less than 1 mg dry weight equivalents per oral dosage unit based on the total dry weight of the *S. repens* herb preparation. In another embodiment, the *S. repens* herb preparation is standardized to contain zinc (e.g., citrate) not less than 5 mg dry weight equivalents per oral dosage unit based on the total dry weight of the *S. repens* herb preparation. In another embodiment, the *S. repens* herb preparation is standardized to contain zinc (e.g., citrate) not less than 7.5 mg dry weight equivalents per oral dosage unit based on the total dry weight of the *S. repens* herb preparation. In another embodiment, the *S. repens* herb preparation is standardized to contain zinc (e.g., citrate) not less than 25 mg dry weight equivalents per oral dosage unit based on the total dry weight of the *S. repens* herb preparation. In another embodiment, the *S. repens* herb preparation is standardized to contain zinc (e.g., citrate) not less than 100 mg dry weight equivalents per oral dosage unit based on the total dry weight of the *S. repens* herb preparation.

In another embodiment, the *S. repens* herb preparation is standardized to contain vitamin D (e.g., cholecalciferol) not less than 1 µg dry weight equivalents per oral dosage unit based on the total dry weight of the *S. repens* herb preparation. In another embodiment, the *S. repens* herb preparation is standardized to contain vitamin D (e.g., cholecalciferol) not less than 5 µg dry weight equivalents per oral dosage unit based on the total dry weight of the *S. repens* herb preparation. In another embodiment, the *S. repens* herb preparation is standardized to contain vitamin D (e.g., cholecalciferol) not less than 7.5 µg dry weight equivalents per oral dosage unit based on the total dry weight of the *S. repens* herb preparation. In another embodiment, the *S. repens* herb preparation is standardized to vitamin D (e.g., cholecalciferol) not less than 25 µg dry weight equivalents per oral dosage unit based on the total dry weight of the *S. repens* herb preparation. In another embodiment, the *S. repens* herb preparation is standardized to vitamin D (e.g., cholecalciferol) not less than 100 µg dry weight equivalents per oral dosage unit based on the total dry weight of the *S. repens* herb preparation.

In certain embodiments, the *Crateva nurvala* extract preparation can be standardized, alone, or in addition to the other herbal preparations also being standardized, as described herein. For example, the *Crateva nurvala* extract preparation can be standardized to have at least one of the following based on total weight of the *Crateva nurvala* root extract preparation: (i) saponins not less than 25%; (ii) tannins not less than 2%; and (iii) lupeol not less than 1.5%.

In one embodiment, the *C. nurvala* herb preparation is standardized to contain not less than about 5% saponins based on the total dry weight of the *C. nurvala* herb preparation. In another embodiment, the *C. nurvala* herb preparation is standardized to contain not less than about 15% saponins based on the total dry weight of the *C. nurvala* herb preparation. In another embodiment, the *C. nurvala* herb preparation is standardized to contain not less than about 25% saponins based on the total dry weight of the *C. nurvala* herb preparation. In another embodiment, the *C. nurvala* herb preparation is standardized to contain not less than about 15% saponins based on the total dry weight of the *C. nurvala* herb preparation. In another embodiment, the *C. nurvala* herb preparation is standardized to contain not less than about 30% saponins based on the total dry weight of the *C. nurvala* herb preparation.

In one embodiment, the *C. nurvala* herb preparation is standardized to contain not less than about 0.5% tannins based on the total dry weight of the *C. nurvala* herb preparation. In another embodiment, the *C. nurvala* herb preparation is standardized to contain not less than about 1% tannins based on the total dry weight of the *C. nurvala* herb preparation. In another embodiment, the *C. nurvala* herb preparation is standardized to contain not less than about 2% tannins based on the total dry weight of the *C. nurvala* herb preparation. In another embodiment, the *C. nurvala* herb preparation is standardized to contain not less than about 4% tannins based on the total dry weight of the *C. nurvala* herb preparation. In another embodiment, the *C. nurvala* herb preparation is standardized to contain not less than about 5% tannins based on the total dry weight of the *C. nurvala* herb preparation.

In one embodiment, the *C. nurvala* herb preparation is standardized to contain not less than about 0.5% lupeol based on the total dry weight of the *C. nurvala* herb preparation. In another embodiment, the *C. nurvala* herb preparation is standardized to contain not less than about 1.5% lupeol based on the total dry weight of the *C. nurvala* herb preparation. In another embodiment, the *C. nurvala* herb preparation is standardized to contain not less than about 3% lupeol based on the total dry weight of the *C. nurvala* herb preparation. In another embodiment, the *C. nurvala* herb preparation is standardized to contain not less than about 5% lupeol based on the total dry weight of the *C. nurvala* herb preparation.

In some embodiments, it is *C. nurvala* and/or *L. aggregata* and/or *S. repens*, and not *E. arvense*, that is standardized. In some other embodiments, all of the four are standardized. In some other embodiments, none of the four is standardized. For example, the herb-containing composition can comprise standardized *C. nurvala* and not standardized *E. arvense*, *L. aggregata*, and *S. repens*. Alternatively, the composition can comprise standardized *E. arvense* and not standardized *S. repens*, *C. nurvala* and *L. aggregata*. Alternatively, the composition can comprise standardized *L. aggregata* and not standardized *S. repens*, *C. nurvala* and *E. arvense*. Alternatively, the composition can comprise standardized *S. repens* and not standardized *L. aggregata*, *C. nurvala* and *E. arvense*. In one embodiment, the composition can comprise standardized *C. nurvala* and *E. arvense* and not standardized *L. aggregata* and *S. repens*. Alternatively, the composition can comprise standardized *C. nurvala* and *L. aggregata*, and not standardized *E. arvense* and *S. repens*. Alternatively, the composition can comprise standardized *E. arvense* and *L. aggregata*, and not standardized *C. nurvala* and *S. repens*. Alternatively, the composition can comprise not standardized *C. nurvala* and standardized *E. arvense*, *L. aggregata*, and *S. repens*. Alternatively, the composition can comprise not standardized *E. arvense* and standardized *S. repens*, *C. nurvala* and *L. aggregata*. Alternatively, the composition can comprise not standardized *L. aggregata* and standardized *S. repens*, *C. nurvala* and *E. arvense*. Alternatively, the composition can comprise not standardized *S. repens* and standardized *L. aggregata*, *C. nurvala* and *E. arvense*. The standardization can be accomplished via any suitable compound, such as silicon, saponins, tannins, lupeol, etc. For example, the *Crateva nurvala* extract preparation can be standardized to have at least one of the following based on total weight of the *Crateva nurvala* root extract preparation: (i) saponins not less than 25%; (ii) tannins not less than 2%; and (iii) lupeol not less than 1.5%. Further, the *Serenoa repens* extract preparation can be standardized to have at least one of the following based on total weight of the *Serenoa repens* extract preparation: (i) about 85% to about 95% fatty acids; (ii) lycopene not less than 750 µg; (iii) zinc (e.g., citrate) not less than 7.5 mg; (iv) selenium (e.g., selenomethionine) not less than 12 µg; and (v) vitamin D (e.g., cholecalciferol) not less than 5 µg.

Other Constituents

The herb-containing compositions described herein can include constituents in addition to the herbal constituents *C. nurvala*, *E. arvense*, *L. aggregata*, and *S. repens*, For example, in one embodiment, the composition can contain silicon, such as in the form of silica, such as anhydrous silica. The additional silicon assists with urogenital tissue support, strengthening and firmness. In one embodiment, the herb-containing composition contains from about 10 mg dry weight equivalents to about 71 mg dry weight equivalents of total silicon per oral dosage unit. In another embodiment, the herb-containing composition contains from about 15 mg dry weight equivalents to about 45 mg dry weight equivalents of total silicon per oral dosage unit. In another embodiment, the herb-containing composition contains from about 28 mg dry weight equivalents to about 34 mg dry weight equivalents of total silicon per oral dosage unit.

In another embodiment, the herb-containing composition contains phosphorous. In one embodiment, the herb-containing composition contains from about 5 mg dry weight equivalents of phosphorous to about 60 mg dry weight equivalents of phosphorous per oral dosage unit. In another embodiment, the herb-containing composition contains from about 10 mg dry weight equivalents of phosphorous to about 50 mg dry weight equivalents of phosphorous per oral dosage unit. In another embodiment, the herb-containing composition contains from about 20 mg dry weight equivalents of phosphorous to about 30 mg dry weight equivalents of phosphorous per oral dosage unit.

In another embodiment, the herb-containing composition contains calcium. In one embodiment, the herb-containing composition contains from about 1 mg dry weight equivalents of calcium to about 30 mg dry weight equivalents of calcium per oral dosage unit. In another embodiment, the herb-containing composition contains from about 5 mg dry weight equivalents of calcium to about 25 mg dry weight equivalents of calcium per oral dosage unit. In another embodiment, the herb-containing composition contains from about 10 mg dry weight equivalents of calcium to about 20 mg dry weight equivalents of calcium per oral dosage unit.

In another embodiment, the herb-containing composition contains magnesium. In one embodiment, the herb-containing composition contains from about 1 mg dry weight equivalents of magnesium to about 30 mg dry weight equivalents of magnesium per oral dosage unit. In another embodiment, the herb-containing composition contains from about 5 mg dry weight equivalents of magnesium to about 25 mg dry weight equivalents of magnesium per oral dosage unit. In another embodiment, the herb-containing composition contains from about 10 mg dry weight equivalents of magnesium to about 20 mg dry weight equivalents of magnesium per oral dosage unit.

The herb-containing composition can take any suitable form, depending on the application. For example, the composition can be a part of a cream. In one embodiment, the herb-containing composition contains from about 1 mg to about 100 mg dry weight equivalents *C. nurvala* stem/bark extract per gram of cream. In another embodiment, the herb-containing composition contains from about 10 mg to about 60 mg dry weight equivalents *C. nurvala* stem/bark extract per gram of cream. In another embodiment, the herb-containing composition contains from about 40 mg to about 60 mg dry weight equivalents *C. nurvala* stem/bark extract per gram of cream.

In another embodiment, the herb-containing composition contains from about 1 mg to about 60 mg dry weight equivalents *E. arvense* herb per gram of cream. In another embodiment, the herb-containing composition contains from about 5 mg to about 40 mg dry weight equivalents *E. arvense* herb per gram of cream. In another embodiment, the herb-containing composition contains from about 10 mg to about 30 mg dry weight equivalents *E. arvense* herb per gram of cream.

In another embodiment, the herb-containing composition contains from about 1 mg to about 60 mg dry weight equivalents *L. aggregata* herb per gram of cream. In another embodiment, the herb-containing composition contains from about 5 mg to about 40 mg dry weight equivalents *L. aggregata* herb per gram of cream. In another embodiment, the herb-containing composition contains from about 10 mg to about 30 mg dry weight equivalents *L. aggregata* herb per gram of cream.

In another embodiment, the herb-containing composition contains from about 1 mg to about 60 mg dry weight equivalents *S. repens* herb per gram of cream. In another embodiment, the herb-containing composition contains from about 5 mg to about 40 mg dry weight equivalents *S. repens* herb per gram of cream. In another embodiment, the herb-containing composition contains from about 10 mg to about 30 mg dry weight equivalents *S. repens* herb per gram of cream.

In one embodiment, the herb-containing composition contains orange oil. In one embodiment, the herb-containing composition contains from about 1 mg to about 30 mg orange oil per gram of cream. In another embodiment, the herb-containing composition contains from about 5 mg to about 25 mg dry orange oil per gram of cream. In another embodiment, the herb-containing composition contains from about 8 mg to about 12 mg orange oil per gram of cream.

In one embodiment, the herb-containing composition contains *Juniperus virginiana* (Cedarwood) stem essential oil. In one embodiment, the herb-containing composition contains from about 1 µg to about 1,000 µg *J. virginiana* stem essential oil per gram of cream. In another embodiment, the herb-containing composition contains from about from about 250 µg to about 750 µg *J. virginiana* stem essential oil per gram of cream. In another embodiment, the herb-containing composition contains from about 400 µg to about 600 µg *J. virginiana* stem essential oil per gram of cream.

In one embodiment, the herb-containing composition contains Myrrh oil. In one embodiment, the herb-containing composition contains from about 1 µg to about 1,000 µg Myrrh oil per gram of cream. In another embodiment, the herb-containing composition contains from about from about 250 µg to about 750 µg Myrrh oil per gram of cream. In another embodiment, the herb-containing composition contains from about 400 µg to about 600 µg Myrrh oil per gram of cream.

In one embodiment, the herb-containing composition contains Orange flower oil. In one embodiment, the herb-containing composition contains from about 1 µg to about 1,000 µg Orange flower oil per gram of cream. In another embodiment, the herb-containing composition contains from about from about 250 µg to about 750 µg Orange flower oil per gram of cream. In another embodiment, the herb-containing composition contains from about 400 µg to about 600 µg Orange flower oil per gram of cream.

In one embodiment, the herb-containing composition contains *Cupressus sempervirens* (Cypress) leaf oil. In one embodiment, the herb-containing composition contains from about 1 µg to about 1,000 µg *C. sempervirens* leaf oil per gram of cream. In another embodiment, the herb-containing composition contains from about from about 50 µg to about 500 µg *C. sempervirens* leaf oil per gram of cream. In another embodiment, the herb-containing composition contains from about 75 µg to about 125 µg *C. sempervirens* leaf oil per gram of cream.

In another embodiment, the herb-containing composition contains d-alpha-tocopheryl acetate (Natural Vitamin E). In one embodiment the herb-containing composition contains d-alpha-tocopheryl acetate. In one embodiment, the herb-containing composition contains from about 0.1 mg to about 25 mg d-alpha-tocopheryl acetate per gram of cream. In another embodiment, the herb-containing composition contains from about 1 mg to about 10 mg dry d-alpha-tocopheryl acetate per gram of cream. In another embodiment, the herb-containing composition contains from about 4 mg to about 6 mg d-alpha-tocopheryl acetate per gram of cream.

In another embodiment, the herb-containing composition contains diazolidinylurea. In one embodiment, the herb-containing composition contains diazolidinylurea. In one embodiment, the herb-containing composition contains from about 0.1 mg to about 10 mg diazolidinylurea per gram of cream. In another embodiment, the herb-containing composition contains from about 1 mg to about 5 mg dry diazolidinylurea per gram of cream. In another embodiment, the herb-containing composition contains from about 3 mg to about 3.5 mg diazolidinylurea per gram of cream.

In another embodiment, the herb-containing composition contains hydroxybenzoates. In one embodiment, the herb-containing composition contains hydroxybenzoates. In one embodiment, the herb-containing composition contains from about 0.1 mg to about 5 mg hydroxybenzoates per gram of cream. In another embodiment, the herb-containing composition contains from about 0.5 mg to about 3 mg dry hydroxybenzoates per gram of cream. In another embodiment, the herb-containing composition contains from about 1 mg to about 2 mg hydroxybenzoates per gram of cream.

In another embodiment, the herb-containing composition contains extracts of C. nurvala stem/bark; E. arvense leaf/stem; L. aggregata root; S. repens leaf/berry; Orange oil; J. virginiana stem; Myrrh oil; Orange flower oil; C. sempervirens leaf; d-alpha-tocopheryl acetate; diazolidinylurea; and hydroxybenzoates.

Medicinal Properties and Uses of Compositions

One embodiment provides herb-containing compositions useful in a method of prophylaxis or treatment of disorders of BPH, e.g., urinary incontinence, enuresis (e.g., bed-wetting), benign prostatic hyperplasia, urinary calculi, cystitis, and UTIs. Not to be bound by any particular theory, but in some embodiments the primary active ingredients present in both the *Crateva* and *Equisetum* are the saponins and plant sterols. *Crateva* contains flavonoids, glucosinolates and the plant sterol, lupeol, while *Equisetum* contains the mineral, silica, flavonoids (isoquercetin, luteolin, and kaempferol) and the saponin, equisetin. Nadkarni K. M. et al., Indian Materia. Medica. Bombay Popular Prakashan; British Herbal Pharmacopeia. Publ: British Herbal Medicine Association 1983; Bone K. *Clinical Applications of Ayurvedic and Chinese Herbs. Monographs for the western herbal practitioner*. Phytotherapy Press, Warwick, Qld, Australia 1997; The German Commission E Monographs, 1998; D'Agostino M. et al., Boll. Soc. Ital. Biol. Sper., 30; 60(12):2241-5 (1984); Pengelly A. *The constituents of medicinal plants: an introduction to the chemistry and therapeutics of herbal medicine*. Sunflower Herbal $2^{nd}$ Edition, Merriwa, NSW, Australia, 1996; Lakshmi V. et al., Planta Medica, 32: 214-216 (1977).

In one embodiment, the herb-containing compositions can be useful in the prevention and treatment of urinary calculi. *Crateva* and *Equisetum* have been shown to alter urinary electrolytes in such a way so as to reduce lithogenic potentiality. Varalakshmi P et al., J. Ethnopharmacology, 28: 313-321 (1990); Anand R. et al., Indian J. Pharmacology, 27: 265-268 (1995); Grases F. et al., Int. Urol. Nephrol., 26(5): 507-511 (1994). *Crateva* has also been found to inhibit small intestinal Na-K-ATPase. Varalakshmi P. et al., J. Ethnopharmacology, 31: 67-73 (1991). These effects may be due primarily to the presence of the sterol lupeol. A number of studies have shown that lupeol has anti-oxaluric and anti-calcuric effects leading to increased spontaneous passing of stones and symptomatic relief. Varalakshmi P et al., J. Ethnopharmacology, 28: 313-321 (1990); Anand R. et al., Indian J. Pharmacology, 27: 265-268 (1995); Malini M. M., et al., Jpn. J. Med. Sci. Biol., 48(5-6):211-20 (1995); Lakshmi V. et al., Planta Medica, 32: 214-216 (1977).

In one embodiment, it is hypothesized that this passage of the stone may be produced via a tonic contractile action of the drug on the smooth muscle. Varalakshmi P et al., J. Ethnopharmacology, 28: 313-321 (1990); Anand R. et al., Indian J. Pharmacology, 27: 265-268 (1995); Deshpande P. J. et al., Indian J. Med. Res., 76(Suppl): 46-53 (1982). *Equisetum* may also assist with incontinence via a similar mechanism. Kaempferol, luteolin and isoquercetin, found in *Equisetum* are documented to inhibit xanthine oxidase and subsequent urate calculi formation. Nagao A. et al., Biosci. Biotechnol. Biochem., 63(10):1787-90 (1999). These herbal drugs can act to improve the tone of the bladder wall. In 1982, Deshpande et al. reported that *Crateva* has beneficial effects on neurogenic bladder and post-prostatectomic atony of the bladder. Deshpande P. J. et al., Indian J. Med. Res., 76(Suppl):46-53 (1982).

In one embodiment, the herb-containing compositions can be useful in the prevention and treatment of incontinence and benign prostatic hypertrophy and urinary incontinence. *Crateva* administration produces a marked relief of symptoms of frequency, incontinence, pain and retention of urine in men with hypotonic bladder as a result of benign prostatic hypertrophy. Deshpande P. J. et al., Indian J. Med. Res., 76 (Suppl):46-53 (1982). *Crateva* can act to increase the tone of the bladder and the expulsive force of urine, thereby helping effective evacuation. Deshpande P. J. et al., Indian J. Med. Res., 76 (Suppl):46-53 (1982)—cystometric studies analyzed in this paper also show that *Crateva* normalizes the tone of the urinary bladder and significantly decreases residual urine volume. The herb-containing compositions provided herein, therefore, are useful in the prevention and treatment of urinary incontinence.

These results are also supported by animal studies where *Crateva* has been shown to increase the tone of both smooth and skeletal muscle in vitro. Das P. K. et al., J. Res. Ind. Med., 9:49 (1974). Animal studies show that 40 days of treatment with *Crateva* resulted in hypertonic curves of the urinary bladder when compared to initial curves. Das P. K. et al., J. Res. Ind. Med., 9:49 (1974).

*Equisetum* is rich in silicic acid and silicates. In one embodiment, silica supports the regeneration of connective tissue. Chevallier, A., *The Encyclopedia of Medicinal Plants*, (Horn V. and Weil, C., Eds.) Dorling Kindersley Ltd., London (1996). Thus, the herb-containing compositions described herein can be useful in the prophylaxis or treatment of disorders of the urogenital system, for example, urinary incontinence, enuresis (e.g., bed-wetting), benign prostatic hyperplasia, urinary calculi, cystitis, and UTIs.

The herb-containing compositions provided herein are useful in the prevention and treatment of UTIs and cystitis. It has been shown in rat studies that some species of the *Equisetum* family have a diuretic action, shown by excretion of sodium, potassium and chloride, similar to that of other drugs such as hydrochlorothiazide. Perez Gutierrez R. M. et al., J. Ethnopharmacol., 14(2-3):269-272 (1985); D'Agostino M. et al., Biol. Soc. Ital. Biol. Sper., 60(12): 2241-5 (1984). A more recent study using rats also demonstrated beneficial affects of the drugs in urolithiasis. Grases F. et al., Int. Urol. Nephrol., 26(5):507-511 (1994). These authors suggest that this result could be due to the antibacterial action of the constituents, namely, the saponins Interestingly, *Crateva* has anti-inflammatory and antibacterial properties. Nadkarni K. M. et al., Indian Materia Medica. Bombay Popular Prakashan; Bone K. *Clinical Applications of Ayurvedic and Chinese Herbs. Monographs for the western herbal practitioner*. Phytotherapy Press, Warwick, Qld, Australia 1997; Salvat A. et al., Lett. Appl. Microbiology, 32(5): 293-7 (2001); Xu H X et al., Phytother. Res., 15(1): 39-43 (2001); Geetha T. et al., Gen. Pharmacol., 32(4):495-7 (1999); Geetha T. et al., J. Ethnopharmacol., 76(1):77-80 (2001). Combined with *Crateva*'s tonic effects on smooth muscle, it is considered to assist with bladder evacuation, thereby decreasing residual urine, a known to contributing factor to UTIs. Deshpande P. J. et al., Indian J. Med. Res., 76(Suppl):46-53 (1982).

Isoquercetin, found in *Equisetum*, is known to have anti-inflammatory effects via inhibition of inflammatory prostaglandins, although *Crateva* is thought to produce anti-inflammatory effects via a different mechanism. D'Agostino M. et al., Boll. Soc. Ital. Biol. Sper., 30; 60(12):2241-5 (1984); Geetha T. et al., Gen. Pharmacol., 32(4):495-7 (1999). The positive effect on chronic urinary tract infections is most likely a combination of anti-bacterial and anti-inflammatory actions.

In one embodiment, the herb-containing compositions can be useful in the prevention and treatment of urinary incontinence, UTIs, and enuresis. There is evidence for the use of Virginia cedarwood in treating incontinence, enuresis and assisting bladder tone as well as bladder infections, difficult urination and cystitis. Tisserand and Balacs, *Essential Oil Safety. A Guide for Health Care Professionals*. Churchill Livingstone, U. K., 1995; 28-29, 31, 33-34; Price, S. Practical Aromatherapy. Thorsons, Harper Collins Publishers, California, U.S., 1983; 157-8, 170-171, 174, 185; Davis, P. *Aromatherapy An A-Z*. The C. W. Daniel Company, Essex, England, 1998; 194; Valnet, J. *The Practice of Aromatherapy*. Saffron Walden, The C. W. Daniel Company, Essex, England, 1980; 120-121; Price, S. *The Aromatherapy Workbook*. Thorsons (Harper Collins), California, USA, 1993; 67; Caddy, R., *Aromatherapy Essential Oils in Colour*. Amberwood Publishing Ltd, East Horsley, Surrey, England, 1997; 14. The documented properties likely to produce this effect include the antispasmodic, diuretic, antiseptic and astringent.

Cypress is documented as an antispasmodic, astringent, antiseptic, deodorant, diuretic and tonic that may promote venous circulation to the kidneys and bladder area, improve bladder tone and assist with urinary incontinence and enuresis. Tisserand and Balacs, *Essential Oil Safety. A Guide for Health Care Professionals*. Churchill Livingstone, U. K., 1995; 28-29, 31, 33-34; Valnet, J. *The Practice of Aromatherapy*. Saffron Walden, The C. W. Daniel Company, Essex, England, 1980; 120-121; Holmes, P. *The Energetics of Western Herbs*. Artemis Press, Boulder, Colo., USA, 1989; 567-569, 792; Damian, P & K. *Aromatherapy Scent and Psyche*. Healing Arts Press, Rochester, Vt., Canada, 1995; 187-188; Price, S. *The Aromatherapy Workbook*. Thorsons (Harper Collins), California, USA, 1993; 67; Chidell, L. *Aromatherapy. A Definitive Guide to Essential Oils*. Hodder and Stoughton Ltd, Kent, UK, 1992; 23-24, 80-81; Keller, E. *The Compete Home Guide to Aromatherapy. H J Kramer, Inc, Tiburon, California, USA,* 1991; 178-179.

Recent literature describes Myrrh as an astringent and antiseptic that produces a soothing effect on mucous membranes of the urinary system and promotes healing of tissues. Battaglia, S. *The Complete Guide to Aromatherapy*. The Perfect Potion Pty Ltd, Virginia, Brisbane, Qld, Australia, 1995; 110-113, 116, 150-151, 158-159, 182-183, 184-185, 187; Lawless, J. *The Encyclopedia of Essential Oils*. (1992) Element Books for Jacaranda Wiley, Ltd, Australia, 1992; 76-77, 88-89, 135-136. Orange and Neroli are documented as having anti-spasmodic, antiseptic and deodorant effects. 6,10; Sheppard-Hanger. *The Aromatherapy Practitioner Manual*. Aquarius Publishing, Willetton, Western Australia, 1995; 183; Sellar, W. *The Directory of Essential Oils*. Saffron Walden, The C.W. Daniel Company, Essex, England, 1992; 50-51, 106-107; Keller, E. *The Compete Home Guide to Aromatherapy*. H J Kramer, Inc, Tiburon, California, USA, 1991; 178-179.

In one embodiment, the herb-containing compositions can be useful in the prevention and treatment of disorders of the prostate, e.g., benign prostatic hyperplasia. Essential oils are also recommended for male reproductive health, indicating a possible effect on the prostate in men. Battaglia, S. *The Complete Guide to Aromatherapy*. The Perfect Potion Pty Ltd, Virginia, Brisbane, Qld, Australia, 1995; 110-113, 116, 150-151, 158-159, 182-183, 184-185, 187; Price, S. *Practical Aromatherapy*. Thorsons, Harper Collins Publishers, California, U.S., 1983; 157-8, 170-171, 174, 185; Lawless, J. *The Encyclopaedia of Essential Oils*. (1992) Element Books for Jacaranda Wiley, Ltd, Australia, 1992; 76-77, 88-89, 135-136; Valnet, J. *The Practice of Aromatherapy*. Saffron Walden, The C. W. Daniel Company, Essex, England, 1980; 120-121.

Certain drugs commonly prescribed for urinary incontinence, such as oxybutynin hydrochloride, inhibit the muscarinic action of acetylcholine on smooth muscle, producing a direct antispasmodic action; that is, they relax the detrusor muscle. Tapp A. J. S. et al., Brit. J. Obstetrics and Gynecology; 97: 521-6 (1990). This antispasmodic effect is preferred to the anticholinergic effect of drugs previously used for patients with urinary incontinence. The antispasmodic effect of these essential oils, whilst not provided in more specific detail, may also be producing an action similar to currently prescribed drug medications.

Herbal diuretics are documented as increasing blood flow through the kidneys without resorption at the distal tubule of the nephron and associated loss of electrolytes (apart from potassium), as is the case with more sophisticated modern drug diuretics. Mills and Bone, *Principles and Practice of Phytotherapy*. Churchill Livingstone, 2000; 35, 220-222. Also, diuresis often does not result from herbal diuretic use. Mills and Bone, *Principles and Practice of Phytotherapy*. Churchill Livingstone, 2000; 35, 220-222. Not to be bound by any particular theory, but it may be that these herbal essential oils largely stimulate the blood flow to the kidneys resulting in an increase or greater efficiency in the production of urine. This effect, when combined with complete emptying of the bladder when voiding, may minimize the volume of urine lost through continual leakage.

Pharmaceutical Compositions and Formulations

One embodiment provides methods of preventing and/or treating BPH-related disorder in a subject by administering to the subject an herb-containing composition in an amount sufficient to prevent or treat the BPH-related disorder (i.e., pharmaceutically effective amount). The composition can be any of the compositions described herein. A subject in need of the presently described composition (and the administration thereof) can be one suffering any of the urogenital system disorders, including at least one of (i) urinary incontinence and (ii) overactive bladder symptoms. For example, the urogenital system disorder can include urinary incontinence, enuresis, benign prostatic hyperplasia, urinary calculi, cystitis, OAB, a urinary tract infection, and the like.

In one embodiment, the herb-containing compositions can be used alone or further formulated with pharmaceutically acceptable compositions, vehicles, or adjuvants with a favorable delivery profile (i.e., suitable for delivery to a subject, particularly one in need thereof). Such compositions typically comprise the herb-containing composition and a pharmaceutically acceptable carrier. "Pharmaceutically acceptable carrier" in some embodiments is intended to include any and all solvents, dispersion media, coatings, antibacterial and antifungal compositions, isotonic and absorption delaying compositions, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. The use of such media and compositions for pharmaceutically active substances is well known in the art. Except insofar as any conventional media or composition is incompatible with the active composition, use thereof in the compositions is contemplated. Supplementary active compositions can also be incorporated into the compositions.

A pharmaceutical composition is formulated to be compatible with its intended route of administration. Examples of routes of administration include, e.g., oral; transdermal (i.e., topical), and transmucosal administration. The pH can be adjusted with acids or bases, such as hydrochloric acid or sodium hydroxide.

Oral compositions generally include an inert diluent or an edible carrier. They can be enclosed in gelatin capsules, caplets or compressed into tablets. For the purpose of oral therapeutic administration, the herb-containing composition can be incorporated with excipients and used in the form of tablets, troches, or capsules. Oral compositions can also be prepared using a fluid carrier for use as a mouthwash, wherein the composition in the fluid carrier is applied orally and swished and expectorated or swallowed. Pharmaceutically compatible binding compositions, and/or adjuvant materials can be included as part of the composition. The tablets, pills, capsules, troches and the like can contain any of the following ingredients, or compositions of a similar nature: a binder such as microcrystalline cellulose, gum tragacanth or gelatin; an excipient such as starch or lactose, a disintegrating composition such as alginic acid, Primogel, or corn starch; a lubricant such as magnesium stearate or Sterotes; a glidant such as colloidal silicon dioxide; a sweetening composition such as sucrose or saccharin; or a flavoring composition such as peppermint, methyl salicylate, or orange flavoring. The herb-containing compositions provided herein can also be formulated as a topical cream for transdermal or transmucosal administration.

In one embodiment, the herb-containing compositions are prepared with carriers that will protect the composition against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

The pharmaceutical compositions can be included in a container, pack, or dispenser together with instructions for administration.

As a result of administrating the presently described herb-containing composition to a subject in need thereof, the symptoms of BPH in the subject can be alleviated. For example, the treatment can result in a reduction in at least one of (i) urinary incontinence and (ii) OAB. In one embodiment, the treatment can result in an improvement of at least one of average daily frequency of urination; average nightly frequency of urination; total urinary incontinence episodes; stress incontinence episodes; and urinary urgency episodes.

In contrast to some of the pre-existing herb-containing compositions, the compositions provided herein surprisingly can provide efficacy and efficiency much higher that the pre-existing compositions. For example, the compositions provided herein can result in improvement that is about at least two times, such as at least three times, four times, five times, or more, as fast as the pre-existing herb-containing compositions. For example, compared to the composition as provided in U.S. Pat. No. 7,378,115, which achieved improvement in about three months, the compositions provided herein can achieve a comparable level of improvement in less than three months, such as less than two months, such as less than one month, such as less than two weeks. In one embodiment, the presently described composition can accomplish the improvement between about two weeks and about two months, such as about two weeks, or such as about one month.

The articles "a" and "an" are used herein to refer to one or to more than one (i.e., to at least one) of the grammatical object of the article. By way of example, "a polymer resin" means one polymer resin or more than one polymer resin. Any ranges cited herein are inclusive. The terms "substantially" and "about" used throughout this Specification are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The invention is further defined by reference to the following examples, which are not meant to limit the scope of the present invention. It will be apparent to those skilled in the art that many modifications, both to the materials and methods, may be practiced without departing from the purpose and interest of the invention.

NON-LIMITING WORKING EXAMPLES

Example 1

Clinical Trial of Herb-Containing Natural Therapeutic Combination for the Treatment of Benign Prostatic Hyperplasia and Related Disorders Summary This study showed that compositions (i.e., Prorox®) containing *Crateva*, Horsetail, *Lindera* and saw palmetto (i.e., *Serenoa repens*) with other nutrients, reduces bladder symptoms associated with BPH, including urinary frequency, urgency, nocturia, and incontinence, without the unwanted side effects and within a 2 to 4 week time frame.

Patients and Methods

Eight adult males with an average age of 54.1 years (range 41-62 years), having medically diagnosed benign prostatic hyperplasia (BPH), were recruited through naturopathic clinics and advertisements in local health food stores in Brisbane, Australia.

All participants entered the study having experienced at least two of the following:
1) frequent urination (more than 10 times daily);
2) urinary urgency (daily);
3) weak urinary stream or stop/start urination (daily);
4) a need to strain or push to begin urination (daily); or
5) nocturia (urination more than once per night).

Further, the participants:
1) had not undergone prostate surgery within the last 12 months;

2) did not have any serious health conditions such as diabetes mellitus, heart disease, pancreatic disease, hepatic disease, or chronic inflammatory conditions;
3) were not being treated for psychotic disturbances;
4) had not used any medicine for BPH symptoms in the month prior to commencement of the study; and
5) did not engage in the specific pelvic exercises to improve muscle tone prior to the study.

The treatment protocol had participants ingest the equivalent of two (2) Prorox® capsules (per day for one month) containing a blend of *Crateva nurvala*, *Equisetum arvense*, *Lindera aggregata*, and saw palmetto (i.e., *Serenoa repens*) with zinc, selenium, lycopene and vitamin D. The efficacy of the treatment was assessed by measuring the average daily and nightly (nocturia) frequency of urination, urinary urgency episodes, the strength of the urine stream, and need for straining during urination. Results were compared to baseline at 2 weeks and again at one month and two months. These results were compared using a paired t-test.

The efficacy of treatment was also assessed and compared to baseline at 2 weeks and at one month and two months by using the International Prostate Symptom Score (IPSS) and a short version of the Urogenital Distress Inventory (UDI). Both the IPSS and UDI are disease specific instruments which provide an efficient tool to detect bladder problems.

The IPSS questionnaire contained eight questions and measured the impact of bladder symptoms associated with BPH. Responses to the first seven symptom questions ranged from 'not at all' with a value of 0 to 'almost always' with a value of 5. Responses to the first seven questions were totaled and rated as follows: 0-7, mildly symptomatic; 8-19, moderately symptomatic; 20-35, severely symptomatic. The IPSS questionnaire also included one quality of life (QOL) question (rated on a 7-point scale from "delighted" to "terrible") about the emotional impact of these bladder symptoms.

The UDI questions related specifically to the physical aspects of BPH, including OAB and incontinence and their effect on QOL. UDI questions were rated on a scale of 0 (not bothered') to 5 (extremely bothered'). Results were analyzed using a paired t-test.

Results and Discussion

Frequency of Urination During the Day

The results demonstrated that the average frequency of urination during the day reduced significantly ($p<0.05$) during the one month of treatment (FIG. 1). The number of times participants needed to empty their bladder reduced from an average of 12.4 times per day (prior to treatment), to 8.9 times per day (after 2 weeks), to 8.1 times per day (after one month), and 7.5 times per day (after 2 months), which is within normal limits.

Frequency of Nocturia

Figure 2:
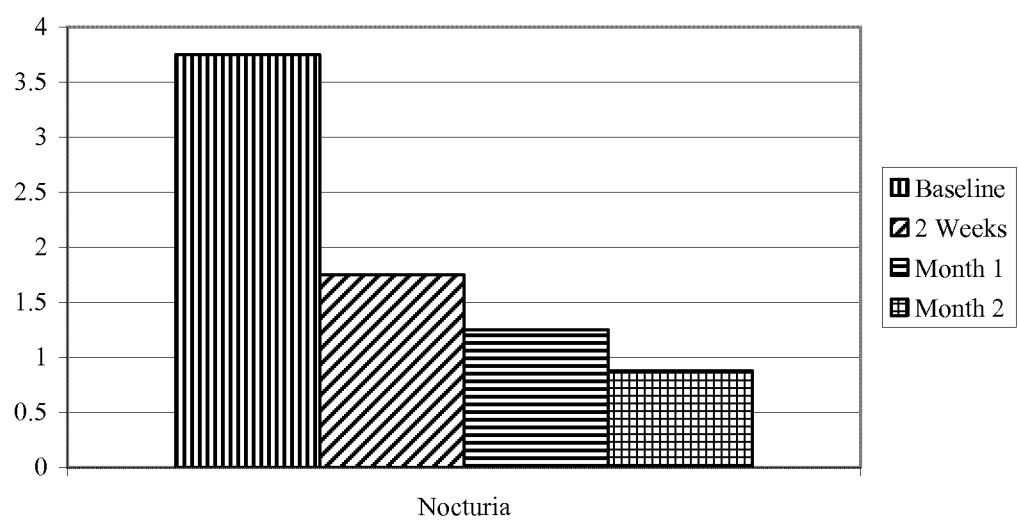
FIG. 2 is a histogram graph showing the frequency that a participant population experienced the symptoms of nocturia (per night) during clinical assessment in one embodiment.

The results demonstrated that this treatment effectively reduced the number of times participants needed to empty their bladder at night (FIG. 2). There was a significant ($p<0.05$) reduction in awakenings from 3.75 times per night initially, to 1.75 times at 2 weeks, to 1.25 times per night at month 1, and 0.88 times per night at month 2, which is within the normal range.

Urinary Urgency

Urinary urgency was significantly reduced from an average of 5 episodes per day to 2.6 times per day (not significant) at 2 weeks to 1.2 times per day ($p=0.025$) at month 1 and less than once a day (5 times per week) at month 2 ($p=0.02$).

Urinary Stream and Straining

There was a slight reduction in weak steam and straining to begin urination; however, these results were not statistically significant. Less than half of the participants experienced these symptoms.

The International Prostate Symptom Score (IPSS)

Figure 3:
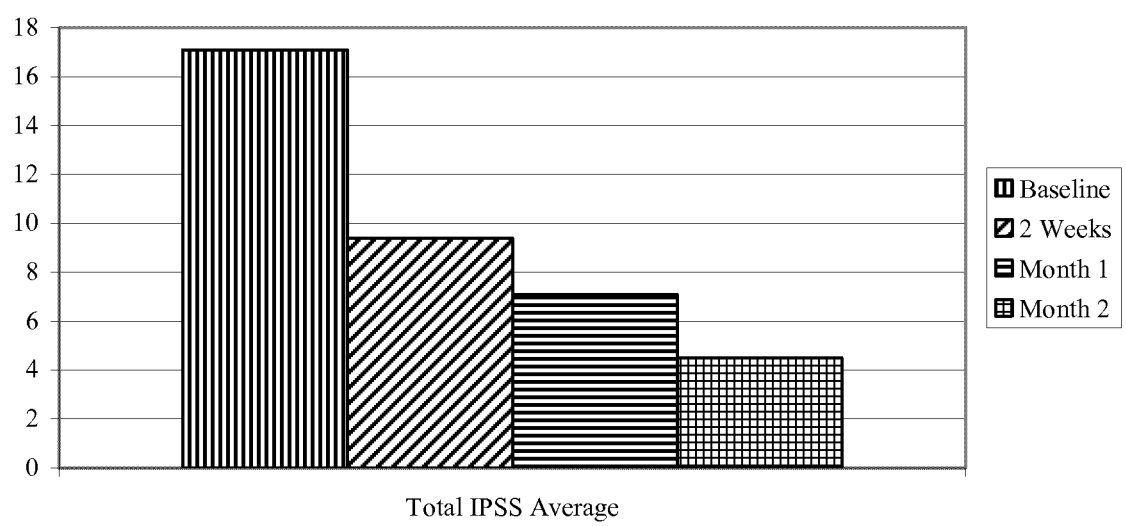
FIG. 3 is a histogram graph showing the average International Prostate Symptom Scores (IPSS) in a participant population in one embodiment.

The total average IPSS score for participants at baseline was 17.1 (ranging from 9 to 30), with all participants categorized as either moderately or severely symptomatic (FIG. 3). At two weeks, the total average IPSS score for participants was significantly ($p<0.05$) reduced to 9.4. IPSS was further reduced to 7.1 at month 1, with participants categorized as mildly to moderately symptomatic, and 4.5 at month 2 (all scores p values<0.001). At month 2, two participants were categorized as moderately symptomatic, five as mildly symptomatic and one participant scored zero (no IPSS score symptoms).

The IPSS score included a question related to the quality of life due to urinary symptoms which asked, 'If you were to spend the rest of your life with your urinary condition just the way it is now, how would you feel about that?' The possible responses were 'delighted, pleased, mostly satisfied, mixed, mostly dissatisfied, unhappy and terrible.' At baseline the average response from participants was between 'mostly dissatisfied' and 'unhappy'. At two weeks and then again and month 1, the average response from participants was closer to 'mostly satisfied'. At month 2, the average response was between 'pleased' and 'delighted'

The Urogenital Distress Inventory (UDI)

Figure 4:
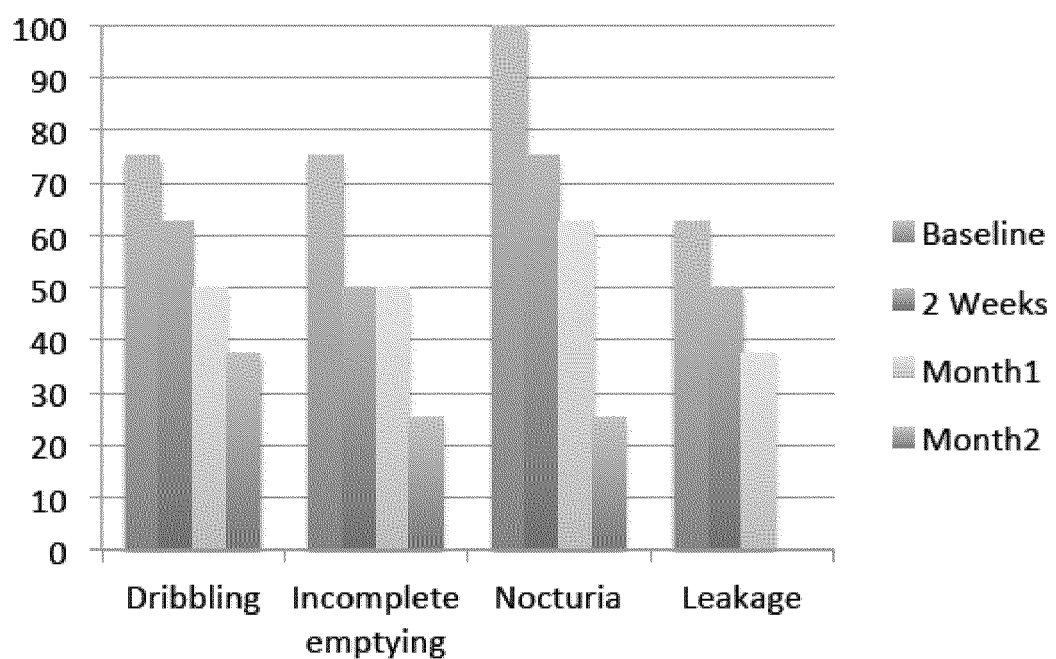
FIG. 4 is a histogram showing the Urinary Distress Index (UDI) by percent affected in one embodiment.

At baseline, the symptoms experienced by most participants included: nocturia (100%), dribbling (75%), incomplete emptying (75%), and leakage (65%). After one month the number of participants bothered by these symptoms was reduced to 62.5%, 50%, 50% and 37.5% respectively. At month 2, the responses had improved further to within the normal range for nocturia and resolution of leakage (FIG. 4).

Conclusion

The results of this study indicated that Prorox® was effective at significantly ($p<0.05$) reducing symptoms of urinary frequency, urgency, and nocturia as well as reducing participants' total average IPSS score. Symptom relief occurred after 2 weeks of treatment, with further improvements at one month. By month 2 urinary frequency in the day and nocturia were within the normal physiological range. Quality of life measures show significant reductions in the percentage of participants feeling bothered by their bladder symptoms. There were no reported side effects. This study showed that Prorox® provides a greater effect than previous herbal formulations in reducing the symptoms of BPH and improving quality of life. Furthermore, these improved results are achieved within a shorter time frame.

Example 2

Patients and Methods

Forty-one adult males with medically diagnosed BPH participated in a trial of either Prorox® or a "Blend" of herbs containing Saw palmetto. Prorox® contains *Crateva* (3 g daily dry herb equivalent (DHE) dose), Horsetail (2 g daily DHE dose), *Lindera* (2 g daily DHE dose), Saw palmetto (3.2 g daily DHE dose) plus nutrients including lycopene, zinc, selenium, and vitamin D. The Blend has a similar dry herb equivalent total dose of herbs, but uses a standardized Horsetail and does not have *Lindera* or vitamin D. In order to directly compare results, participant's percent (%) reduction in the frequency of urination, nocturia and total IPSS scores for each formulation was used. This method of analysis was used because baseline (at Month 0) values varied in each of the studies.

Results And Discussion

The percentage of people on each formula that experienced symptoms at Month 1 was assessed and compared. Comparison of the frequency of urination and nocturia indicated that Prorox® was more effective in reducing the frequency of urination during the day (34% reduction at month 1 for Prorox® compared to 18% reduction at month 1 for the Blend). Prorox® was also superior to the Blend in reducing nocturia with a 67% reduction at month 1 for Prorox® compared to 27% reduction at month 1 for the Blend. See Table 3, below.

TABLE 3

Percent Decrease in Frequency of Urination

|  | Day | | Night | |
| --- | --- | --- | --- | --- |
|  | The Blend | Prorox ® | The Blend | Prorox ® |
| Month 0 vs Month 1 | 18 | 34 | 27 | 67 |

Figure 5:
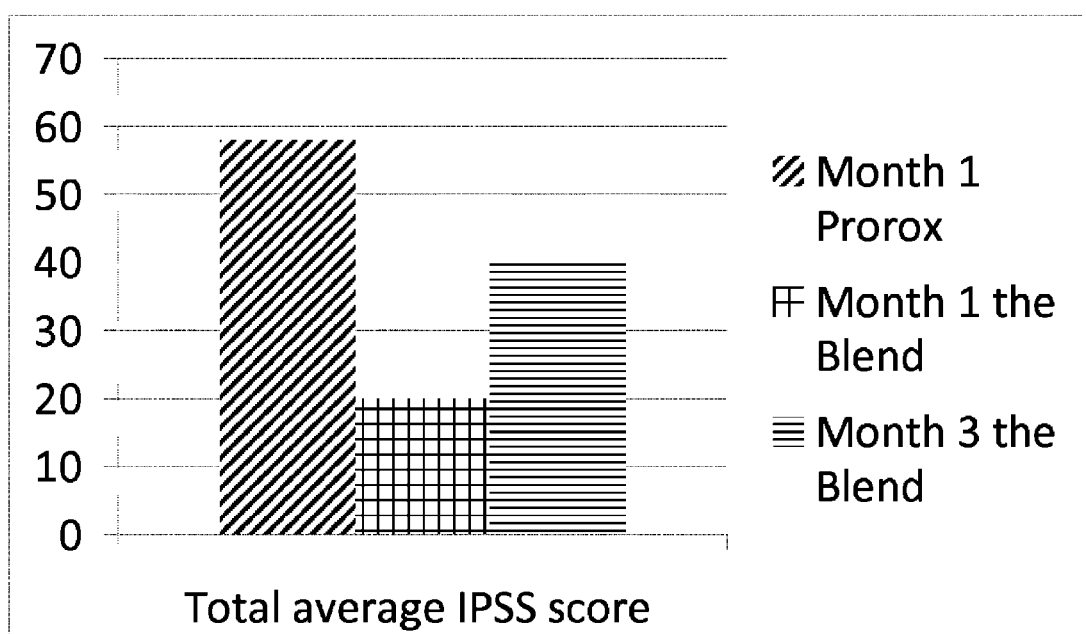
FIG. 5 is a histogram graph showing the effects of Prorox® vs a blend of herbs containing saw palmetto upon percentage (%) reduction in total IPSS scores in a participant population in one embodiment.

The results of the total IPSS score percentage (%) reduction was also assessed and compared. These results indicated that Prorox® had a greater effectiveness at month 1. Furthermore, the results for Prorox® at Month 1 were comparable to or better than the Month 3 results for the Blend. This showed that Prorox® produced results within a shorter time frame. See Table 4, below, and (FIG. 5).

TABLE 4

|  | Prorox ® Month 1 | The Blend Month 1 | The Blend Month 3 |
| --- | --- | --- | --- |
| Frequent Urination | 34 | 18 | 35 |
| Nocturia | 67 | 27 | 62 |
| Total average IPSS score | 58 | 20 | 40 |

Conclusion

The results of this study indicated that Prorox® was safe and not associated with major adverse reactions. It effectively reduced symptoms of daytime urinary frequency and nocturia, and reduced total average IPSS scores.

The reduction in symptoms was faster and more marked for Prorox® than for the Blend after month 1 of treatment. Prorox® provided a greater reduction in urinary frequency during the day (34% versus 18% reduction) and at night (67% versus 27% reduction) at month 1 and improved the total average IPSS score (58% versus 20%). Results produced by Prorox® after one month of treatment were comparable to or better than results from the Blend after 3 months of treatment.

In summary, compositions containing *Crateva*, Horsetail, *Lindera*, saw palmetto (i.e., *Serenoa repens*) and nutrients provided greater and faster effectiveness in reducing symptoms of BPH when compared to earlier herbal combinations shown to be effective in this area.

Example 3

PROROX Case Studies

Recent research is indicating that up to 40% of men who think they have BPH (benign prostatic hyperplasia) may actually have OAB (overactive bladder; urinary, frequency, urgency, nocturia and urge incontinence). Prorox® targets the bladder and prostate to encompass the variety of causes for the bladder symptoms in the ageing male.

Bladder symptoms for most men using Prorox® start improving within 2-4 weeks. This is faster than treatments that focus specifically on the prostate and supports the view that the bladder may be a primary cause for many of these men. The following cases were with men who used Prorox for 2 months.

Case 1

A 60 year old male presented with urinary frequency, 12 times daily, and urinary urgency with each micturition. He was quite concerned about his bladder symptoms. Weak stream and the need to strain or push to start urination occurred one third of the time. Additionally, he had nocturia 5 times per night.

His urinary symptoms had started at age 40. His physician initially suspected a urinary tract infection and prescribed antibiotics, which had no effect. Subsequent examination indicated benign prostate enlargement so over the years he ingested a variety of herbal supplements, including pygeum, nettle, and saw palmetto, with varying but incomplete effects.

Within two weeks of using Prorox®, his IPSS (International Prostate Symptom Score) score went from 30 (severely symptomatic) to 19 (moderately symptomatic) and all urinary parameters improved. Patient continued Prorox® use and at 2 months his urinary frequency was normal (7 per day), and his nocturia (2 per night) and his IPSS (score of 13) were dramatically reduced.

Case 2

59 year old male presented with nocturia, 3 times nightly, and urinary urgency and straining with each micturition. For the past year he has experienced the above symptoms and incontinence episodes with the urinary urgency. His IPSS score was 18 (moderate) at the start of treatment.

After 2 weeks of treatment with Prorox®, his straining and urgency was reduced to 1 in 4 micturitions and nocturia to 2 per night. His IPSS was reduced to 14 (moderate). By 1 month, his IPSS was 9 (moderate), urgency occurred once per day, and nocturia occurred once per night. By 2 months of treatment, his urinary symptoms were all within normal parameters with nocturia once per night, and IPSS of 2 (mild).

Case 3

A 65 year old farmer with urinary frequency (12 times daily). His frequency was worse in the morning, where he would urinate approximately every hour. His symptoms would vary but were worse if he awoke with a headache and took acetaminophen (paracetamol). Symptoms were also worse with coffee. He had nocturia, 3 times nightly, as well as a weak urinary stream and urinary urgency until early afternoon. His PSA was 23 (severe).

After two weeks of treatment with Prorox®, he had a reduction in all urinary parameters and his IPSS reached 15. His symptoms continued to improve and by 2 months his urinary frequency was 9 per day and nocturia once per night. He had no need for straining to start urination, no incontinence and his urinary urgency would occur one third of the time. His IPSS score was 10 (moderate) at 2 months.

REFERENCES

1. Desphande P. J, Sahu M, Kumar P, 1982. *Crataeva nurvala* Hook and Forst (Varuna) the Ayurvedic drug of choice in urinary disorders. Indian Journal of Medical Research; 76 (Suppl) December: 46-53.

2. Blumenthal, M., ed., 1998. The Complete German Commission E Monographs. American Botanical Council. Austin, Tex.:

3. The British Herbal Pharmacopeia. Publ: Brisbane Herbal Medicine Association, 1983.

4. Bensky D and Gamble A, 1993. *Chinese Herbal Materia Medica*, Revised Edition. England Press, Seattle, Wash., USA.

5. Schauss A G, Spiller G, Chaves S, Gawlicka A, 2006. Reducing the symptoms of overactive bladder and urinary incontinence: results of a two-month, double-blind, placebo-controlled clinical trial. Poster presentation FASEB, San Francisco, April, 2006.

6. Steels E, Ryan J, Seipel T, Rao A, 2002. *Crateva* and *Equisetum* reduce urinary incontinence symptoms. *Australian Continence Journal;* 8 (3).

7. Niederprym, H. J., Schweikert. H. U., ZŠnker, K. S. Testosterone 5 alpha-reductase inhibition by free fatty acids from *Sabal serrulata* fruits. Phytomedicine 1994; 1:127-133.

8. Sultan, C., et. Al, 1984 Inhibition of androgen metabolism and binding of liposterolic extract of *Serenoa repens* B in human foreskin fibroblasts. Journal of Steroid Biochemistry. 1984; 20(1):515-519.

9. Weissner, H., et. Al, 1996. Effects of the *Sabal serrulata* extract IDS 9 and its subfractions on 5 alpha-reductase activity in human benign prostate hypertrophy. The Prostate; 28:300-06.

10. Tasca, A., et. Al, 1985. Treatment of obstructive symptomatology caused by prostate adenoma with an extract of *Serenoa repens*. Double-blind clinical study vs. placebo. Minerva Urologica e Nefrologica; 37:87-91.

11. Crimi, A., Russo, A, 1983. The use of *Serenoa repens* extract in the treatment of functional disturbances caused by prostate hypertrophy. Medical Praxis; 4: 47-51.

12. Braeckman, J, 1994. The extract of *Serenoa repens* in the treatment of benign prostate hypertrophy: a multicenter open study. Current Therapeutic Research; 55(7): 776-85.

13. Boyle P, Robertson C, Lowe F, Roehrborn C, 2004. Updated meta-analysis of clinical trials of *Serenoa repens* extract in the treatment of symptomatic benign prostate hypertrophy. British Journal of Urology; 93(6):751-6.

14. Gong E M, Gerber G S, 2004. Saw palmetto and benign prostate hypertrophy. American Journal of Chinese Medicine; 32(3):331-8.

15. Nagaraj M, Sunitha S, Varalakshmi P, 2000. Effect of lupeol, a pentacyclic triterpene, on the lipid peroxidation and antioxidant status in rat kidney after chronic cadmium exposure. *Journal of Applied Toxicology;* 20(5): 413-417.

16. Ohno T, Takemura G, Murata I, Kagawa T, Akao S, Minatoguchi S, Fujiwara T and Fujiwara H, 2005. Water extract of the root of *Lindera* strychnifolia slows down the progression of diabetic nephropathy in db/db mice. *Life Sciences;* 77(12):1391-1403.

17. Geetha T, Varalakshmi P, 2001. Anti-inflammatory activity of lupeol and lupeol linoleate in rats. *Journal of Ethnopharmacology;* 76(1): 77-80.

18. Geetha T, Varalakshmi P, 1999. Anticomplement activity of triterpenes from *Crataeva nurvala* stem bark in adjuvant arthritis in rats. *General Pharmacology;* 32(4):495-7.

19. Yubin Luo, Mei Liu, Xiujuan Yao, Yufeng Xia, Yue Dal, Guixin Chou and Zhengtao Wang, 2009. Total alkaloids from Radix Linderae prevent the production of inflammatory mediators in lipopolysaccharide-stimulated RAW 264.7 cells by suppressing NF-κB and MAPKs activation. *Cytokine;* 46(1): 104-110.

20. Qinglin L, Guixin C, Changgui D, Zhengtao W, Fang H, 1997-12. Studies on the analgesic and anti-inflammatory action of radix Linderae extract. *Journal of Chinese Medicinal Materials*. (China Pharmaceutical University, Nanjing 210038) (Abstract)

21. Badmaev, V., Majeed, M., Passwater, R, 1996. Selenium: A quest for better understanding. Alternative Therapies; 2(4):59-67.

22. Compare F, Mahmoud A, 2004. Preventing diseases of the prostate in the elderly using hormones and nutriceuticals. Aging Male; 7(2):155-69.

23. Cristoni A, Di Pierro F, Bombardelli E, 2000. Botanical derivatives for the prostate. Fitoterapia; 71(1):521-8.

24. Lagiou P, Wuu J, Trichopoulou A, Hsieh C C, Adami H O, Trichopoulou D, 1999. Diet and benign prostatic hyperplasia: a study in Greece. Urology; 54(2):284-90.

25. Zachara B A, Szewczyk-Golec K, Tyloch J, Wolski Z, Szylberg T, Stepien S, Kwiatkowski S, Blach-Boguslawaska E, Wasowicz W, 2005. Blood and tissue selenium concentrations and glutathione peroxidase activities in patients with prostate cancer and benign prostate hyperplasia. Neoplasma; 52(3):248-54.

26. Tuohimaa P, Lyakhovich A, Aksenov N, Pennanen P, Syvälä H, Lou Y, M. Ahonen M, Hasan T, Pasanen P, Blauer M, Manninen T, Miettinen S, Vilja P and Ylikomi T, 2001. Vitamin D and prostate cancer. The Journal of Steroid Biochemistry and Molecular Biology; 76 (1-5): 125-134.

27. Swami S, Krishnan A and Feldman D, 2011. Article in Press. Review: Vitamin D metabolism and action in the prostate: Implications for health and disease. Molecular and Cellular Endocrinology. Available online 28 Barry M et al., 2011. Effect of increasing doses of Saw palmetto extract on the lower urinary tract symptoms. Journal of the American Medical Association; 306(12): 1344-1351.

29. Anand R, Patnaik G K, Kamal Roy, Bhaduri A P, 1995. Antioxaluric and anticalciuric activity of lupeol derivatives. *Indian Journal of Pharmacology;* 27: 265-268.

30. Grases F, Melero G. Costa-Bauza A, Prieto R, March J G, 1994. Urolithiasis and phytotherapy. *International Journal of Urology and Nephrology;* 26(5): 507-511.

31. Varalakshmi P, Shamila Y, Latha E. Effect of *Crataeva nurvala* in experimental urolithiasis. J Ethnopharmacology 1990; 28: 313-321.

32. Malini M M, Baskar R, Varalakshmi P. Effect of lupeol, a pentacyclic triterpene, on urinary enzymes in hyperoxaluric rats. Jpn J Med Sci Biol 1995 October-December; 48(5-6): 211-20.

33. Das P K, Rathor R S, Lal R, Tripathi R M, Ram A K, Biswas M, 1974. Anti-inflammatory and anti-arthritic activity of Varuna. *Journal of Research of Indian Medicine;* 9:49.

34. Nagao A, Seki M, Kobayashi H, 1999. Inhibition of xanthine oxidase by flavonoids. Biosci *Biotechnology Biochemistry;* 63(10): 1787-90.

35. Robinson D, Pearce K F, Preisser J S, Dugan E, Suggs P K and Cohen S J, 1998. Relationship between patient reports of urinary incontinence symptoms and quality of life measures. Obstetrics and Gynaecology; 91 (2): 224-228.

36. Coyne K, Payne C, Bhattacharyya S, Revicki D, Thompson C, Corey R, Hunt T, 2004. The impact of urinary urgency and frequency on health-related quality of life in overactive bladder: Results from a national community survey. *Value in Health;* 7(4)

37. Bone K. Clinical Applications of Ayurvedic and Chinese Herbs, 1997. *Monographs for the western herbal practitioner*. Phytotherapy Press, Warwick, Queensland, Australia.

38. Chan Wang, Yue Dai, Jian Yang, Guixin Chou, Changhong Wang, Zhengtao Wang, 2007. Treatment with total alkaloids from Radix Linderae reduces inflammation and joint destruction in type II collagen-induced model for rheumatoid arthritis. *Journal of Ethnopharmacology;* 111: 322-328.

39. Runwei Yan, Yang Yang, Yingying Zeng, Guolin Zou, 2009. Cytotoxicity and antibacterial activity of *Lindera* strychnifolia essential oils and extracts. *Journal of Ethnopharmacology;* 121: 451-455.

40. Shimomura M, Ushikoshi H, Hattori A, Murata I, Ohm Y, Aoyama T, Kawasaki M, Nishigaki K, Takemura G, Fujiwara T, Fujiwara H, Minatoguchi S, 2010. Treatment with *Lindera* strychnifolia reduces blood pressure by decreasing sympathetic nerve activity in spontaneously hypertensive rats. *American Journal of Chinese Medicine;* 38(3): 561-8.

41. Noda Y, Mori A, Anzai K, Packer L, 1999. Superoxide anion radical scavenging activity of Uyaka (*Lindera* strychnifolia), a natural extract used in traditional medicine. Antioxidant Food Supplements in Human Health.

42. Bin Li, Gil-Saeng Jeong, Dae-Gill Kang, Ho-Sub Lee and Youn-Chul Kim, 2009. Cytoprotective effects of lindenenyl acetate isolated from *Lindera strychnifolia* on mouse hippocampal HT22 cells. *European Journal of Pharmacology.* Neuropharmacology and Analgesia; 16(1-3): 58-65.

The invention is further defined by reference to the following examples, which are not meant to limit the scope of the present invention. It will be apparent to those skilled in the art that many modifications, both to the materials and methods, may be practiced without departing from the purpose and interest of the invention.

EQUIVALENTS

This invention has been described in terms of specific embodiments set forth in detail herein, but it should be understood that these are by way of illustration and the invention is not necessarily limited thereto. Modifications and variations will be apparent from the disclosure and may be resorted to without departing from the spirit of the invention as those of skill in the art will readily understand. Accordingly, such variations and modifications are considered to be within the purview and scope of the invention and the following claims.

What is claimed:

1. An herb-containing composition, comprising:
   (i) a *Crateva nurvala* extract preparation of about 4 g to about 8 g dry weight equivalents;
   (ii) an *Equisetum arvense* extract preparation of about 2 g to about 4 g dry weight equivalents;
   (iii) a *Lindera aggregata* extract preparation of about 2 g to about 4 g dry weight equivalents; and
   (iv) a *Serenoa repens* extract preparation of about 3 g to about 8 g dry weight equivalents;
   wherein the herb-containing composition is formulated as an oral dosage consisting of capsules, tablets or caplets.

2. The herb-containing composition of claim 1, wherein the *Crateva nurvala* extract preparation of about 4.5 g to about 7.5 g dry weight equivalents, the *Equisetum arvense* extract preparation of about 2.5 g to about 3.5 g dry weight equivalents, the *Lindera aggregate* extract preparation of about 2.5 g to about 3.5 g dry weight equivalents, and the *Serenoa repens* extract preparation of about 3.5 g to about 7.5 g dry weight equivalents.

3. The herb-containing composition of claim 1, wherein the *Crateva nurvala* extract preparation of about 5 g to about 7 g dry weight equivalents, the *Equisetum arvense* extract preparation of about 2.6 g to about 3.4 g dry weight equivalents, the *Lindera aggregata* extract preparation of about 2.6 g to about 3.4 g dry weight equivalents, and the *Serenoa repens* extract preparation of about 4 g to about 7 g dry weight equivalents.

4. The herb-containing composition of claim 1, wherein the *Crateva nurvala* extract preparation of about 5.5 g to about 6.5 g dry weight equivalents, the *Equisetum arvense* extract preparation of about 2.7 g to about 3.3 g dry weight equivalents, the *Lindera aggregata* extract preparation of about 2.7 g to about 3.3 g dry weight equivalents, and the *Serenoa repens* extract preparation of about 4.5 g to about 6.5 g dry weight equivalents.

5. The herb-containing composition of claim 1, wherein the composition has at least one of the following:
   (i) the *Crateva nurvala* extract preparation is a stem/bark extract preparation;
   (ii) the *Equisetum arvense* extract preparation is a stem extract preparation;
   (iii) the *Lindera aggregata* extract preparation is a root extract preparation; and
   (iv) the *Serenoa repens* extract preparation is a leaf/berry extract preparation.

6. The herb-containing composition of claim 1, wherein the herb-containing composition is formulated in a dry delivery system.

7. The herb-containing composition of claim 1, wherein the herb-containing composition is formulated in a liquid delivery system.

8. The herb-containing composition of claim 1, wherein the herb-containing composition is formulated in a controlled-release vehicle.

9. A pharmaceutical composition comprising the herb-containing composition of claim 1 and a pharmaceutically-acceptable carrier.

10. An herb-containing composition comprising:
    (i) a *Crateva nurvala* stem/bark extract preparation of about 4 g to about 8 g dry weight equivalents;
    (ii) the *Equisetum arvense* stem extract preparation of about 2 g to about 4 g dry weight equivalents;
    (iii) the *Lindera aggregate* root extract preparation of about 2 g to about 4 g dry weight equivalents; and
    (iv) the *Serenoa repens* leaf/berry extract preparation of about 3 g to about 8 g dry weight equivalents,
    wherein the herb-containing composition is formulated as an oral dosage unit consisting of capsules, tablets or caplets; and
    wherein *Lindera aggregata* is concentrated to an extract ratio of at least about 5:1.

11. The herb-containing composition of claim 10, wherein the composition contains at least 1,500 mg dry weight equivalents of *Crateva nurvala* stem/bark.

12. The herb-containing composition of claim 10, wherein the composition contains at least 1,000 mg dry weight equivalents of *Equisetum arvense* stem extract and *Lindera aggregate* root extract.

13. The herb-containing composition of claim 10, wherein the composition contains at least 3,200 mg dry weight equivalents of *Serenoa repens* leaf/berry extract.

14. A pharmaceutical composition comprising the herb-containing composition of claim 10 and a pharmaceutically-acceptable carrier.

15. The herb-containing composition of claim 10, wherein the oral dosage unit is selected from the group consisting of: a tablet and capsule.

* * * * *